United States Patent
Ohashi et al.

(10) Patent No.: US 6,603,060 B1
(45) Date of Patent: Aug. 5, 2003

(54) METHOD FOR REGULATING CELL DEATH

(75) Inventors: Yuko Ohashi, Tsukuba (JP); Shigemi Seo, Tsukuba (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 0 days.

(21) Appl. No.: 09/192,056

(22) Filed: Nov. 13, 1998

(30) Foreign Application Priority Data

Mar. 11, 1998 (JP) .......................................... 10-060158

(51) Int. Cl.⁷ .......................... C12N 15/82; C12N 5/10; A01H 1/00; A01H 5/00
(52) U.S. Cl. ...................... 800/279; 800/278; 800/283; 800/286; 800/289; 800/290; 800/300; 800/301; 435/320.1; 435/419; 435/468
(58) Field of Search ................................ 800/278, 279, 800/283, 286, 289, 290, 300, 301; 435/320.1, 419, 468

(56) References Cited

PUBLICATIONS

Dangle Et Al. The Plant Cell. 1996. vol. 8:1793–1807.*
The Biological Review (The Zn Finger Homedomain's Reference Retrieved on Sep. 27, 2000, Retrieved from the Internet:<URL:http://sdb.bio.purdue.edu/fly/gene/zinchf1.1.htm).*
Hugueney, P. et al. *Proc. Nat. Acad. Sci. USA* 92:5630–34 (1995).
Shimomura, T. et al. *Virology,* vol. 43, pp. 531–532 (1971).
Ohashi, T. et al. *Virology,* vol. 48, pp. 601–603 (1972).
Lindahl, M. et al. *The Journal of Biological Chemistry,* vol. 271, pp. 29329–29334 (1996).
Nakai, T. et al. *Molecular and Cellular Biology,* vol. 15, pp. 4441–4452 (1995).
Zamzami, N. et al. *J. Exp. Med.,* vol. 181, pp. 1661–1672 (1995).
Krippner, A. et al. *The Journal of Biological Chemistry,* vol. 271, pp. 21629–21636 (1996).
Quillet–Mary, A. et al. *The Journal of Biological Chemistry,* vol. 272, pp. 21388–21395 (1997).
Adam, Z. *Plant Molecular Biology,* vol. 32, pp. 773–783 (1996).
Holmes, F.O. *Phytopathology,* vol. 28, pp. 553–561 (1938).

* cited by examiner

*Primary Examiner*—Amy J. Nelson
*Assistant Examiner*—Cynthia Collins
(74) *Attorney, Agent, or Firm*—Townsend and Townsend and Crew LLP

(57) ABSTRACT

A method for regulating cell death in a plant, includes the steps of: transforming a plant cell with a polynucleotide containing a gene encoding DS9 or a homologue thereof or a part of the gene; and redifferentiating the transgenic plant cell to obtain a plant. The DS9 or the homologue thereof is an ATP-dependent Zn-type metalloprotease. The polynucleotide decreases or increases production of the ATP-dependent Zn-type metalloprotease in the plant cell, whereby cell death of a cell in the plant is promoted or suppressed.

4 Claims, 9 Drawing Sheets (7 of 9 Drawing Sheet(s) Filed in Color)

H, H2O; E, EDTA; D, DCMU

FIG. 11
Amount of DS9 protein in DS9-introduced tobacco
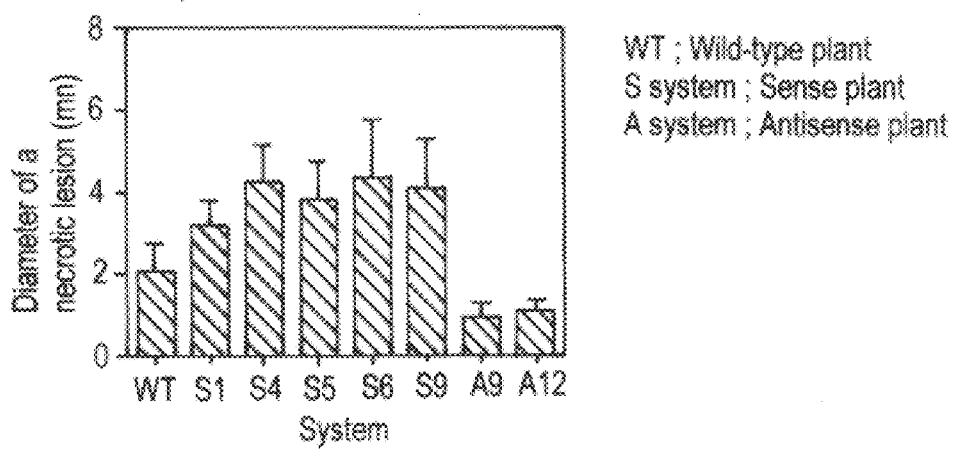
WT ; Wild-type plant
S system ; Sense plant
A system ; Antisense plant
FIG. 12
Diameter of a necrotic lesion in DS9-introduced tobacco 5 days after TMV inoculation
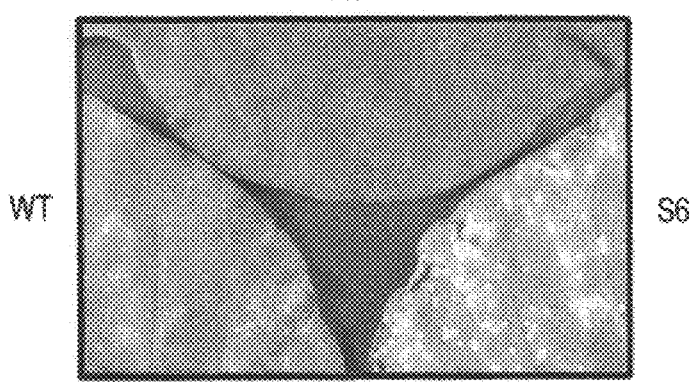
WT ; Wild-type plant
S system ; Sense plant
A system ; Antisense plant
FIG. 13

METHOD FOR REGULATING CELL DEATH

BACKGROUND OF THE INVENTION

1. Field of the Invention

The present invention relates to a method for regulating cell death. More specifically, the present invention relates to a method for providing a plant to which is conferred resistance to various environmental stresses by regulating an expression level of a cell death regulatory gene.

2. Description of the Related Art

When a plant is infected with a pathogen, e.g., virus, bacteria, filamentous fungi, and viroid, the plant shows either of the following reactions: 1) allowing pathogen to grow by spreading through the entire body of the plant, whereby the plant gets disease or 2) enclosing pathogen in an infected site so as to prevent if from spreading through the entire body of the plant, whereby the plant is provided with resistance to the pathogen. The latter reaction of a plant against the pathogen is called a hypersensitive response or reaction (HR). It is known that, in this reaction, cell death locally occurs in an infected site to form necrotic lesions. Such a formation of necrotic lesions involved in pathogen infection is a typical resistance reaction of a plant, which is considered as an example of programmed cell death. However, the molecular mechanism of this reaction remains unclear.

The HR does not occur in all plants. The HR is believed to occur when a plant intrinsically contains a gene which recognizes a product of a pathogenic gene derived from infecting pathogen. In the case where such a gene is not present, the HR does not occur, and a plant is not resistant against the pathogen infection.

The HR of tobacco against tobacco mosaic virus (TMV) infection is a model system which has been conventionally used for studying the HR of a plant.

An N gene is one of the cell death regulatory genes involved in the HR (i.e., cell death) due to TMV infection. It is reported that tobacco having the N gene (NN tobacco) shows the HR against TMV infection, but tobacco having no N gene (nn tobacco) does not show the HR (Holmes, Phytopathology, 28, 553, (1938)). The HR of the NN tobacco occurs only at 24° C. or lower. It does not occur at 28° C. or higher. Therefore, it has been considered that both the N gene and the temperature condition are required for inducing the HR in a TMV-infected cell.

However, the inventors' group has found that, in the case where the NN tobacco is treated with actinomycin D (AMD) and heat (50° C., 2 minutes), the HR is induced in the NN tobacco against TMV infection even under the temperature condition of 30° C. at which the HR does not usually occur. Furthermore, the HR was also induced against TMV infection in the nn tobacco having no N gene, in the case where the nn tobacco was similarly treated with AMD and heat. Because of this, it was clarified that cell death against TMV infection may occur irrespective of the presence or absence of the N gene and the temperature condition (Shimomura and Ohashi, Virology, 43, 531, (1971); Ohashi and Shimomura, Virology, 48, 601 (1972)). It is known that AMD inhibits DNA-dependent RNA synthesis in a nucleus (Reich et al., Proceedings of the National Academy of Sciences, 48, 1238 (1962)). Thus, a possibility was shown that a novel cell regulatory gene may be present in a plant, and that the HR may be induced by suppression of transcription of the gene, followed by suppression of synthesis of proteins.

It is considered that if the above-mentioned cell death regulatory gene is identified, cell death of a plant can be regulated (promoted or suppressed) by controlling an expression level of the gene. In particular, it is an important task in the agricultural field to provide a plant which is conferred with resistance to environmental stress by regulating cell death.

However, the cell death regulatory gene as described above has not been identified. To the extent that the inventors are aware, there has been no study for providing a plant which is conferred environmental-stress resistance by regulating an expression level of such a gene to promote or suppress cell death.

SUMMARY OF THE INVENTION

The present invention provides a method for regulating cell death in a plant of the present invention including the steps of: transforming a plant cell with a polynucleotide containing a gene encoding DS9 or a homologue thereof or a part of the gene; and redifferentiating the transformed plant cell to obtain a plant, wherein the DS9 or the homologue thereof is an ATP-dependent Zn-type metalloprotease, and the polynucleotide decreases or increases production of the ATP-dependent Zn-type metalloprotease in the plant cell, whereby cell death of a cell in the plant is promoted or suppressed.

A polynucleotide containing a gene encoding DS9 or a homologue thereof or a part thereof may be incorporated into a DNA in a nucleus of a plant cell by a known gene recombinant technique. The term "polynucleotide" refers to a polymer of nucleotides, and is not limited to a particular chain length.

In one embodiment of the present invention, the polynucleotide contains the gene encoding the DS9 or the homologue thereof or the part of the gene in an antisense orientation, whereby cell death of a cell in the plant is promoted.

A method for producing a plant which is conferred with resistance to environmental stress of the present invention includes the steps of: transforming a plant cell with a polynucleotide containing a gene encoding DS9 or a homologue thereof or a part of the gene; and redifferentiating the transformed plant cell to obtain a plant, wherein the DS9 or the homologue thereof is an ATP-dependent Zn-type metalloprotease, and the polynucleotide decreases or increases production of the ATP-dependent Zn-type metalloprotease in the plant cell.

In one embodiment of the present invention, the environmental stress is pathogen infection.

In another embodiment of the present invention, the polynucleotide contains the gene encoding the DS9 or the homologue thereof or the part of the gene in an antisense orientation.

In another embodiment of the present invention, the homologue has a homology of about 70% or more with respect to an ATPase region of the DS9.

In a method for screening a selective inhibitor of a gene encoding DS9 or a homologue thereof of the present invention, the DS9 or the homologue thereof is an ATP-dependent Zn-type metalloprotease, wherein the method includes the steps of: introducing a candidate inhibitor into an expression system having a gene encoding the DS9 or the homologue thereof; and identifying whether or not production of the DS9 or the homologue thereof is selectively decreased in the expression system.

Thus, the invention described herein makes possible the advantages of (1) providing a method for promoting or suppressing cell death by regulating an expression level of a cell death regulatory gene; and (2) providing a method for producing a plant which is conferred with resistance to environmental stress, e.g., pathogen infection, by regulating cell death; and (3) providing a method for screening a selective inhibitor of a cell death regulatory gene.

These and other advantages of the present invention will become apparent to those skilled in the art upon reading and understanding the following detailed description with reference to the accompanying figures.

BRIEF DESCRIPTION OF THE DRAWINGS

The patent or application file contains at least one drawing executed in color. Copies of this patent with color drawing (s) will be provided by the Patent and Trademark Office upon request and the payment of the necessary fee.

FIG. 6A is an electron microscope photograph showing DS9 protein localization in a mesophyll cell treated with an anti-DS9 antibody and anti-rabbit IgG conjugated with 10 nm-gold particles. A horizontal bar in the figure represents 1 μm. FIG. 6B is an electron microscope photograph showing FIG. 6A in a higher magnification. The horizontal bar represents 0.1 μm. FIG. 6C is an electron microscope photograph of a mesophyll cell treated with non-immunized serum (control) and anti-rabbit IgG conjugated with 10 nm-gold particles. The horizontal bar represents 0.1 μm. FIG. 6D is an electron microscope photograph showing DS9 localization in a frozen section of a mesophyll cell treated with an anti-DS9 antibody and anti-rabbit IgG conjugated 10 nm-gold particles. The horizontal bar represents 0.1 μm.

FIG. 11 is an electrophoresis photograph showing the results of western blotting analysis for tobacco with a DS9 gene introduced thereto in a sense (S) or antisense (A) orientation. This analysis represents the amount of DS9 protein in the transgenic tobacco. Anti-DS9 antibody was used for the analysis. Wild-type tobacco was used as a control regarding the amount of protein.

FIG. 12 is a graph showing diameters of necrotic lesions in tobacco with a DS9 gene introduced thereto in a sense (S) or antisense (A) orientation. The necrotic lesions were obtained 5 days after TMV inoculation in the transgenic tobacco. Wild-type tobacco was used as a control.

FIG. 13 is a photograph of morphology representing necrotic lesions in tobacco (A9 and S6) with a DS9 gene introduced thereto in a sense (S) and antisense (A) orientation. The necrotic lesions were obtained 5 days after TMV infection of the transgenic tobacco. Wild-type tobacco was used as a control.

DESCRIPTION OF THE PREFERRED EMBODIMENTS

DS9 is one of ATP-dependent Zn-type metalloprotease newly isolated from a higher plant. The inventors have shown that DS9 and homologues thereof are a cell death-regulating factor. This regulation is conducted, for example, by suppressing production of DS9 or a homologue thereof under environmental stress, which results in induction of cell death of a plant cell. The present invention is based on this novel finding.

The inventors isolated 6 clones which are expressed in a manner specific to the occurrence of the HR in tobacco. One of the isolated clones was designated as a "DS9 gene", and its entire base sequence was determined.

Figure 3:
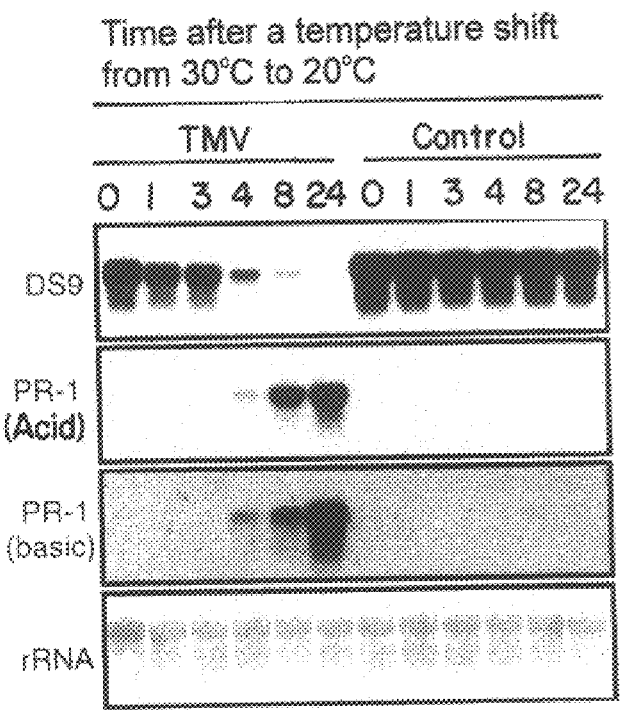
FIG. 3 is an electrophoresis photograph showing the results of northern analysis for NN tobacco infected with TMV. This analysis exhibits fluctuations in DS9 transcription after the temperature shift from 30° C. to 20° C. As a control for fluctuations, wounded leaves were used as a mock. rRNA was measured as a control for expression. As a control for showing degree of the HR, PR-1 gene was measured. PR-1 gene is specifically expressed during infection. Each number on the top of the figure denotes the time after the temperature shift from 30° C. to 20° C.
Figure 4:
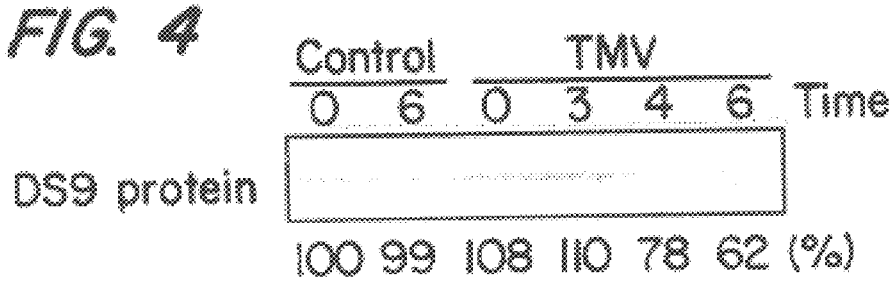
FIG. 4 is an electrophoresis photograph showing the results of western blotting analysis for NN tobacco infected with TMV. This analysis exhibits fluctuations in the amount of DS9 protein after the temperature shift from 30° C. to 20° C. As a control for fluctuations, wounded leaves were used as a mock. Anti-DS9 antibody was used afor the analysis. Each number in the upper portion of the figure denotes the time after the temperature shift from 30° C. to 20° C. Each number in the lower portion of the figure denotes the amount of the protein at each time, with the amount of the protein at the 0th time after the mock infection being 100%.

Based on a deduced amino acid sequence encoded by the DS9 gene, a homologous gene was searched. As a result, the DS9 amino acid sequence was found to show 40%, 30%, 80%, and 42% homology with the respective amino acid sequences of the following ATP-dependent Zn-type metalloproteases: FtsH from *E. coli*, Osdlp from yeast, ArFtsH from Arabidopsis, and Pftf from red pepper. In particular, a high homology was found in a conserved region specific to ATPase. Table 1 shows the comparison in the amino acid sequence among DS9 used in the present invention (SEQ ID NO:3); FtsH from *E. coli* (SEQ ID NO:5), Osdlp from yeast (SEQ ID NO:6), ArFtsH from Arabidopsis (SEQ ID NO:4); and Pftf from red pepper (SEQ ID NO:7). Each amino acid is represented by the one letter code.

lation product (FIGS. 3 and 4). In a leaf of NN tobacco infected with TMV, the transcription level and the amount of the protein were decreased within one hour after the temperature shift from 30° C. to 20° C. On the other hand, in a leaf subjected to mock infection, the transcription level of the DS9 gene and the amount of protein were constant (see Examples 4 and 6). Furthermore, when the leaf subjected to mock infection were treated with actinomycin D (AMD) and heat shock (HS) which are known to induce the HR, the amount of the DS9 protein was remarkably decreased (see Example 7).

Based on the above experimental results, the inventors confirmed that the DS9 is a factor having a function of regulating cell death in a plant, and conducted various experiments for the purpose of developing the method for using the DS9. As a result, the following was found.

TABLE 1

Walker motif A

| | | | | | | | |
|---|---|---|---|---|---|---|---|
| DS9 | KNPDKYTALG | AKIPKGCLLV | GPPGTGKTLL | ARAVAGEAGV | PFFSCAASEF | VELFVGVGAS | 332 |
| ArFtsH | .......... | .......... | .......... | .......... | ....SRPQ.. | .......... | 341 |
| FtsH | RE.SRFQK.. | G.....V.M. | .......... | .K.I....K. | ...TISG.D. | ..M....... | 231 |
| Osdlp | .D.T..ES.. | G.L...V..T | .......... | ...T...... | D..FMSG... | D.VY.....K | 360 |
| Pftf | .K.ERF..V. | .R....V... | .......... | .K.I...... | ....ISG... | ..M....... | 309 |

Walker motif B

| | | | | | | | |
|---|---|---|---|---|---|---|---|
| DS9 | RVRDLFEKAK | SKAPCIVFID | EIDAVGRQRG | AGMGGGNDER | EQTINQLLTE | MDGFSGNSGV | 392 |
| ArFtsH | .......... | .......... | .......... | .......... | .......... | .......... | 401 |
| FtsH | ...M..Q.. | KA....I... | .......... | ..L...H... | ......M.V. | ....E..E.I | 291 |
| Osdlp | .I....AQ.R | .R..A.I... | .L..I.GKRN | P---KDQAYA | K..L....V. | L....QT..I | 417 |
| Pftf | ......K... | EN.......V. | .......... | T.I....... | ...L...... | ....E..T.I | 369 |

SRH

| | | | | | | | |
|---|---|---|---|---|---|---|---|
| DS9 | IVLAATNRPD | VLDSALLRPG | RFDRQVTVDR | PDVAGRIKIL | QVHSRGKALA | KDVDFEKIAR | 452 |
| ArFtsH | .......... | .......... | .......... | ......V... | .........G | .....D.V.. | 461 |
| FtsH | ..I....... | ...P...... | ......V.GL | ...R..EQ.. | K..M.RVP.. | P.I.AAI... | 351 |
| Osdlp | .IIG...F.E | A..K...... | ...KV.N..L | ...R..AD.. | KH.MKKIT.. | DN..PTI... | 477 |
| Pftf | ..V.....A. | I......... | ......S..V | ..IK..TE.. | K..AGN.KFD | S...SL.V..M | 429 |

| | | | | | | | |
|---|---|---|---|---|---|---|---|
| DS9 | RTPGFTGADL | QNLMNEAAIL | AARRELKEIS | KNEISDALER | IIAGPEKKNA | VVSEEKKKLV | 512 |
| ArFtsH | .......... | .......... | ....DV.... | .D........ | .......... | .......R.. | 521 |
| FtsH | G....S.... | A..V....LF | ...GNKRVV. | MV.FEK.KDK | .MM.A.RRSM | .MT.AQ.EST | 411 |
| Osdlp | G...LS..E. | A..V.Q..VY | .CQKNAVSVD | MSHFEW.KDK | .LM.A.R.TM | .LTDAARKAT | 537 |
| Pftf | .....S.... | A..L...... | .G..GKTA.A | SK..D.SID. | .V..M.-GTV | MTDGKS.S.V | 488 |

Zn-binding motif

| | | | | | | | |
|---|---|---|---|---|---|---|---|
| DS9 | AYHEAAHALV | GALMPEYDPV | PKISIIPRGQ | AGGLTFFAPS | EERLESGLYS | RSYLENQMAV | 572 |
| ArFtsH | .....G.... | A......... | .......... | .......... | .......... | .......... | 581 |
| FtsH | .....G..II | .R.V..H... | H.VT.....R | .L.V...L.E | GDAISA---. | .QK...S.IST | 468 |
| Osdlp | .F...G..IM | AKYTNGAT.L | YKAT.L...R | .L.I..QL.E | MDKVDI---T | KRECQARLD. | 594 |
| Pftf | .Y..VG..IC | .TLT.GH... | Q.VTL..... | .K...W.I.A | DDPTLI---. | KQQ.FARIVG | 545 |

Figure 1:
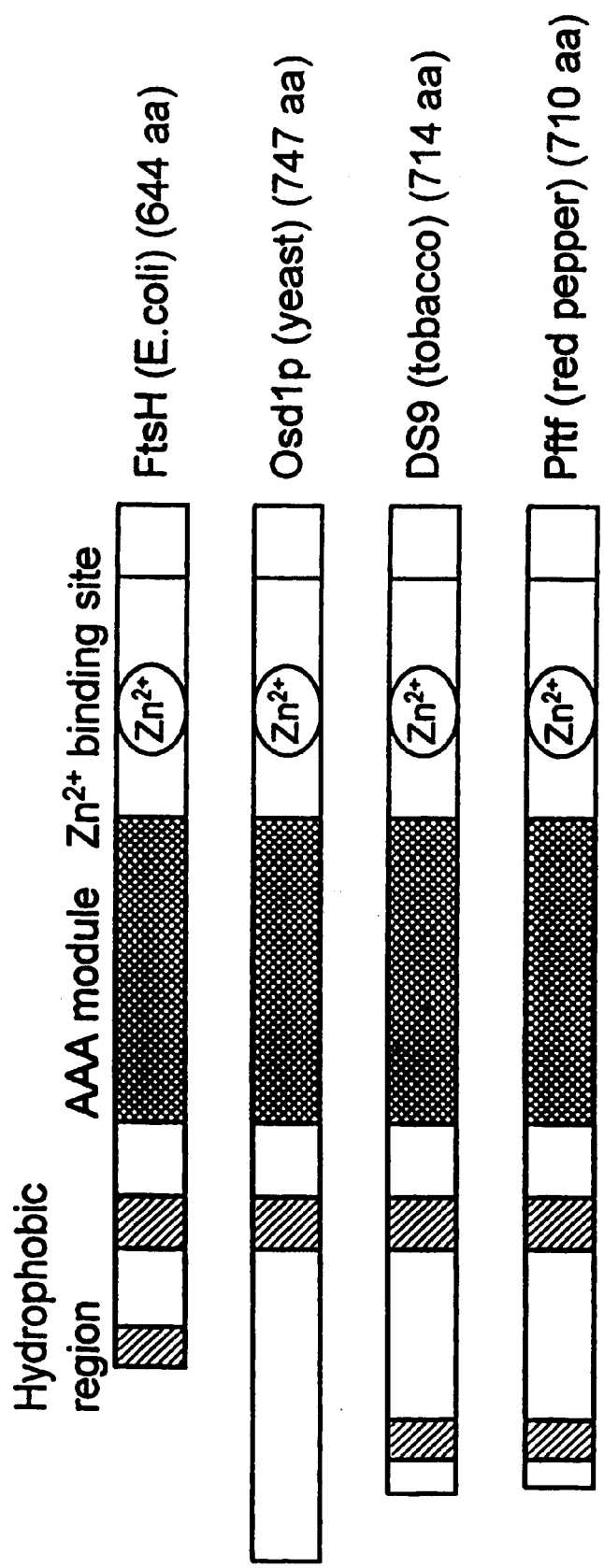
FIG. 1 is a schematic diagram showing a structural comparison between DS9 and other ATP-dependent Zn-type metalloproteases. The DS9 includes a hydrophobic region on the N-terminus, an ATPase region in the middle, and a $Zn^{2+}$ binding motif on the C-terminus, as in the other ATP-dependent Zn-type metalloproteases. The hydrophobic region is considered to be a trans-membrane region.
Figure 2:
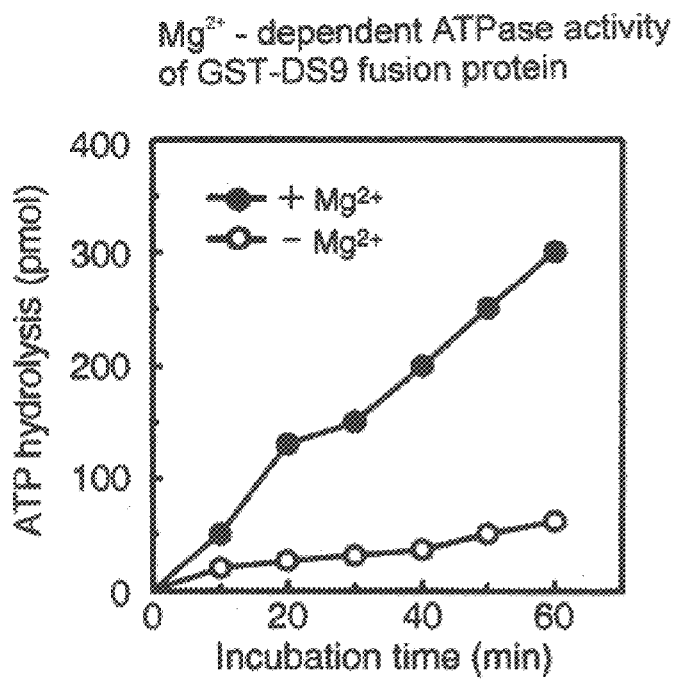
FIG. 2 is a graph showing $Mg^{2+}$-dependent ATPase activity of GST-DS9 fusion protein.

As in the other ATP-dependent Zn-type metalloproteases, the DS9 includes hydrophobic regions (in Table 1, represented by "Walker motif A" and "Walker motif B"), which are considered to penetrate a membrane, near the N-terminus, an ATPase region (represented by "SRH") in the middle portion, and a $Zn^{2+}$ binding motif near the C-terminus (FIG. 1). Furthermore, the DS9 recombinantly expressed in *E. coli* actually exhibited ATPase activity (FIG. 2). These results show that the DS9 used in the present invention is an ATP-dependent Zn-type metalloprotease.

As a result of analysis on the function of the DS 9 gene when the HR was induced, it was shown that the DS9 gene was suppressed until the HR occurred, for both the transcription level and the amount of a protein that is a trans- 1) As a result of testing the effects of various protease inhibitors in inducing the formation of necrotic lesions, it was shown that cell death was induced in TMV-infected tobacco only in the case of using a metalloprotease inhibitor.

2) The DS9 was found to be localized in chloroplast.

3) The HR was induced in cases of both the metalloprotease inhibition and the decrease in a function of chloroplast, even when a temperature was not shifted in a manner known to be needed for the HR to occur.

4) The decrease in a function of the chloroplast, which was observed upon induction of the HR, was related to the decrease in the amount of the DS9 protein.

5) Cell death was promoted in a plant in which the DS9 gene was introduced in an antisense orientation so as to decrease the transcription level of the DS9 gene and the amount of the protein. This antisense plant acquired resistance to pathogen.

6) Cell death was suppressed in a plant in which the DS9 gene was introduced in a sense orientation so as to increase the transcription level of the DS9 gene and the amount of protein. This sense plant acquired resistance to a superoxide-generating herbicide.

FtsH, a homologue of the DS9, is derived from a bacterium. It is interesting that the DS9 was found in chloroplast, which is considered to be derived from a bacterium, in terms of considering its origin. It is reported that ArFtsH, another homologue of the DS9, is also localized in chloroplast (Lindahl et al., The Journal of Biological Chemistry, Vol. 271, pp. 29329–29334 (1996)). Thus, a possibility is suggested that a homologue of the DS9 generally functions in chloroplast. Furthermore, it is assumed that the DS9 and a homologue thereof function in a mitochondrion which is also considered to be derived from a bacterium. Actually, it is shown that a FtsH homologue is involved in decomposition of unfolded subunit 2 of cytochrome C oxidase in yeast mitochondria (T. Nakai et al., Mol. Cell. Biol., 15, 4441–4452 (1995)).

It is reported that in mammals, apoptosis is caused by the decrease in a membrane electric potential due to the inhibition of an electron-transport system in mitochondria. The decrease in the membrane electric potential is inhibited by Bcl-2 or the like which is the product of a cell death regulatory gene (N. Zamzami et al., Exp. Med., 181, 1661–1672 (1995)). Furthermore, it is reported that cell death is caused in the case where an electron-transport system does not successfully function in mitochondria in mammals (Kripper et al., The Journal of Biological Chemistry, 271, 21629, (1996) and Quillet-Mary et al., The Journal of Biological Chemistry, 272, 21388, (1997)). On the other hand, it is reported that a certain kind of protease works to maintain homeostasis in chloroplast (Zatch Adam, Plant Molecular Biology, 32, 773–783, (1996)).

Considering the above, the mechanism of cell death which is regulated in the present invention can be explained as described below. It should be noted that the scope of the method of the present invention is not limited or bound by the following mechanism.

The DS9 or a homologue thereof, which is a metalloprotease, decomposes unfolded proteins or abnormal proteins, thereby maintaining homeostasis of chloroplast and mitochondria. When a plant is placed under environmental stress, transcription of a gene encoding the DS9 or a homologue thereof in chloroplast and mitochondria is suppressed. As a result, in some tissues, the protein level of a translation product (and thus activity level of the metalloprotease) decreased. In these tissues, cell death is induced as shown by the inventors. That is, when unfolded proteins or abnormal proteins increase and accumulate in the chloroplast and mitochondria, they serve to decrease the function (i.e., ATP or NADPH production) of chloroplast and mitochondria. In chloroplast, where photosynthesis is conducted, light energy cannot be processed successfully in chloroplast due to the decrease in this function. As a result, active oxygen is generated in a plant cell. Such a collapse of homeostasis in a cell (i.e., collapse of an electron-transport system and resultant accumulation of active oxygen) eventually leads to cell death. It is considered that the DS9 or a homologue thereof decomposes the above-mentioned unnecessary proteins to save cells from death and functions so as to maintain homeostasis.

Accordingly, in view of various factors as mentioned above, it is expected that the similar mechanism of cell death may exist not only in plant cells, but in eucaryocytes in general.

Hereinafter, the present invention will be described in more detail.

As described above, the inventors revealed a function of a cell death regulatory gene which promotes or suppresses cell death depending upon its expression level. The present invention is based on this finding.

According to the present invention, a method for promoting or suppressing cell death by regulating an expression level of a cell death regulatory gene is provided. Furthermore, according to the present invention, a method for producing a plant which is conferred with resistance to various environmental stress by regulating cell death is provided.

The term "cell death regulatory gene" as used herein refers to a gene which promotes or suppresses cell death depending upon its expression level. According to the present invention, a gene encoding the DS9 and a homologue thereof and a part of the gene are contemplated to be the cell death regulatory genes.

As used herein, the term "expression" of a gene refers to transcription of DNA into mRNA. The degree of transcription to mRNA is represented by an expression level. Thus, suppression of transcription refers to the decrease in an expression level, and promotion of transcription refers to the increase in an expression level.

The term "DS9" as used herein refers to an ATP-dependent Zn-type metalloprotease having an amino acid sequence represented in SEQ ID NO:1 of Sequence Listing. The term "ATP-dependent Zn-type metalloprotease" refers to a protease which requires ATP for its enzyme activity and contains a divalent metal ion (typically, $Zn^{2+}$) in an active center. This enzyme includes, in its amino acid sequence, one or more hydrophobic region near the N-terminus, a metal ion binding region (typically, a $Zn^{2+}$ binding region) near the C-terminus, and an ATPase region in the middle portion. Typically, the enzyme includes two hydrophobic regions near the N-terminus and a $Zn^{2+}$ binding region near the C-terminus.

The term "homologue of the DS9" as used herein refers to an ATP-dependent metalloprotease similar to the DS9, which is a protein having a homology of at least about 30%, preferably at least about 40%, with respect to the entire amino acid sequence of the DS9. Furthermore, the term "homologue of the DS9" refers to a protein having a homology of at least about 60%, preferably at least about 70% with respect to the amino acid sequence in the ATPase region of the DS9. Examples of the homologue include FtsH from E. coli, Osdlp from yeast, ArFtsH from Arabidopsis, and Pftf from red pepper.

As a method for isolating a naturally occurring gene encoding the DS9 and a homologue thereof, for example, a differential screening effective for cloning a gene which expresses a variable amount of mRNA can be used. A method for producing a gene library for conducting differential screening, stringent conditions used for hybridization with a probe, and a method for cloning a gene are well-known to those skilled in the art. For example, see Maniatis et al., Molecular Cloning, A Laboratory Manual, 2nd Ed., Cold Spring Harbor Laboratory Press, Cold Spring Harbor, N.Y. (1989).

A novel gene encoding a homologue of the DS9 can also be used as a cell death regulatory gene. Such a novel gene can be obtained from various gene libraries of organisms, using a gene encoding the DS9 or a known homologue thereof, or a fragment of the gene as a probe. For example, a gene library of a plant, a gene library of *E. coli,* and a gene library of yeast can be used. Stringent conditions for screening a library are appropriately selected by those skilled in the art.

It can be easily determined whether or not an amino acid sequence encoded by the obtained gene corresponds to a homologue of the DS9. Such determination can be carried out by aligning the amino acid sequence encoded by the obtained gene with the amino acid sequence of the DS9 by using commercially available computer analysis software (e.g., Gene Works (IntelliGenetics, Inc.)), and investigating the homology therebetween.

As a gene encoding the DS9 or a homologue thereof, or a part of the gene, an artificially synthesized gene or a part thereof, as well as a naturally occurring gene can be used. Hereinafter, the subject gene will be interchangeably referred to as a "DS9-related gene".

The term "a part thereof" as used herein refers to a fragment of the gene used in the present invention having a length sufficient for reproducing the cell death regulatory function of the DS9 or a homologue thereof.

The term "a part thereof" in the case where a DS9-related gene is introduced in an antisense orientation refers to a fragment having complementation and length sufficient for an antisense RNA produced to contain the said part to inhibit translation of mRNA which is a sense strand in a plant. The fragment has a homology, as a sense strand, of typically about 50%, preferably about 80%, more preferably about 90%, and most preferably about 95% or more in a nucleotide sequence level with a region complementary to an endogenous DS9-related gene present in the plant. The length of the fragment is typically at least about 20 nucleotides, preferably at least about 50 nucleotides, more preferably at least about 100 nucleotides, and most preferably at least about 200 nucleotides.

The term "a part thereof" in the case where a DS9-related gene is introduced in a sense orientation refers to a fragment of the gene including a sequence encoding a region sufficiently extended, such that an expression product, i.e., a part of the DS9 or a homologue thereof exhibits metalloprotease activity. This fragment preferably encodes a metal ion binding region and an ATPase region of a metalloprotease. More preferably, the fragment further encodes a signal region for localizing the expression product in a cell organelle of interest.

A DS9-related gene or a part thereof can be introduced into a plant through an appropriate plant expression vector integrated in a sense or antisense orientation depending upon the purpose of regulation of cell death. In the case where a DS9-related gene or a part thereof is introduced in an antisense orientation, cell death is typically promoted. In the case where a DS9-related gene or a part thereof is introduced in a sense orientation, cell death is typically suppressed. However, it is well-known in the art that co-suppression may occur depending upon the expression level of an introduced gene. The co-suppression is a phenomenon in which, as a result that mRNA of an introduced gene is excessively produced, the expression level of the introduced gene and a homologous, endogenous gene are both suppressed. When the co-suppression occurs, the expression level of a DS9-related gene may be suppressed, thereby promoting cell death.

As is appreciated by those skilled in the art, in the case where the co-suppression allows the effects of the present invention to be obtained, the above-mentioned "part thereof" introduced in a sense orientation may not be needed to encode a region sufficient for exhibiting metalloprotease activity. In this case, the definition of the "part thereof" with respect to the antisense orientation is applied.

The "plant" to which the method of the present invention is applied includes both monocotyledon and dicotyledon. Examples of the particularly preferable plants include tobacco, green pepper, eggplant, melon, tomato, sweet potato, cabbage, spring onion, broccoli, carrot, cucumber, citrus fruit, Chinese cabbage, lettuce, peach, rice, potato, barley, flour, and apple. Unless otherwise indicated, a plant as used herein includes any one of a plant body, a plant organ, a plant tissue, a plant cell, and a seed. Examples of the plant organ include a root, a leaf, a pedicle, and a flower. Examples of the plant cell include callus and a suspension culture cell.

It may be preferable, but not required, that a cell death regulatory gene which can be used in the method of the present invention is derived from a plant of the same species as, or of species related to, that of a plant of interest (e.g., species classified into the same genus or family).

The term "polynucleotide" as used herein has a DS9-infected gene or a part thereof, and any additional sequence required for achieving desired transformation. The polynucleotide is typically in the form of a plant expression vector.

The "plant expression vector" as used herein refers to a recombinant construct of a nucleic acid sequence in which various regulatory elements, such as a promoter for regulating the expression level of a gene of interest, are linked to the gene or to each other in such a manner as to be operable in a host plant cell. Preferably, the plant expression vector may include a plant promoter, a terminator, a marker gene such as a drug resistant gene, and an enhancer. More preferably, the plant expression vector may include an origin of replication. It is well-known to those skilled in the art that the type of a plant expression vector and the preferable kind of a regulatory element may be varied depending upon a host cell.

According to the present invention, those skilled in the art can regulate the degree of cell death by appropriately selecting a regulatory element such as a promoter and an enhancer.

The plant expression vector used in the present invention may further contain a T-DNA region. The T-DNA region allows a gene to be efficiently introduced into a plant genome, especially when Agrobacterium is used to transform a plant.

The term "plant promoter" as used herein refers to a promoter capable of functioning in a plant cell. Examples of the plant promoters include, but are not limited to, promoters whose expressions are induced by a certain kind of stress, for example, a promoter of a gene encoding an infection specific protein PR-1 of tobacco (hereinafter, referred to as "tobacco PR-1 promoter") and promoters whose expressions are induced by heat shock, or constitutive promoters such as a Cauliflower mosaic virus (CaMV) 35S promoter and a promoter of nopaline synthase (Pnos).

The term "terminator" as used herein refers to a sequence positioned downstream of a region of a gene encoding a protein, which is involved in the termination of transcription of mRNA, and the addition of a poly A sequence. The terminator is known to contribute to the stability of mRNA, thereby affecting the expression level of a gene. Examples of the terminator include, but not limited to, a CaMV 35S terminator, a terminator of a nopaline synthase gene (Tnos), and a terminator of a tobacco PR-1 gene.

The "drug resistance gene" is desirable to facilitate the selection of the transgenic plant. As the drug resistance gene, a neomycin phosphotransferase II (NPTII) gene for conferring kanamycin resistance, a hygromycine phosphotransferase gene for conferring hygromycine resistance, and the like are preferably used.

Examples of promoters for expressing the drug resistance gene include, but are not limited to, the above-mentioned plant promoters such as a tobacco PR-1 promoter, a CaMV 35S promoter, and a nopaline synthase promoter.

An enhancer may be used to enhance expression of a gene of interest. As the enhancer, an enhancer region containing a sequence upstream of the above-mentioned CaMV 35S promoter is preferable. A plurality of enhancers may be used per one gene of interest.

A vector used in the present invention for constructing a plant expression vector may preferably be a pBI-type vector, a pUC-type vector, or a pTRA-type vector.

The pBI-type and pTRA-type vectors may introduce a gene of interest, using Agrobacterium, into a plant. A pBI-type binary vector or an intermediate vector may be preferably used. Examples of the pBI-type vector include pBI121, pBI101, pBI101.2 and pBI101.3. These vectors contain a gene from a T-DNA region, which can be introduced into a plant via Agrobacterium mediated transformation. These vectors also contain a NPTII gene which confers kanamycin resistance to a plant. The NPTII gene is expressed under the control of a plant promoter to serve as a marker gene.

Use of the pUC-type vector may allow a gene to be directly introduced into a plant. Examples of the pUC-type vector include pUC18, pUC19 and pUC9.

The plant expression vector of the present invention can be produced by using a gene recombinant technique well-known to those skilled in the art. Preferably, a DS9-related gene or a part thereof is incorporated downstream of a promoter of the vector in a sense or antisense orientation.

A plant expression vector is introduced into a plant cell by using methods well-known to those skilled in the art, for example, a method of infecting a plant cell with Agrobacterium or a method of directly introducing a plant expression vector into a plant cell. As a method for introducing a plant expression vector into a plant cell via Agrobacterium, for example, the method of Nagel et al. (Micribiol. Lett., 67, 325 (1990)) can be used. According to this method, for example, first, Agrobacterium is transformed with a plant expression vector by, for example, electroporation, and then, the transformed Agrobacterium is introduced into a plant cell in accordance with a method described in Plant Molecular Biology Manual (S. B. Gelvin et al., Academic Press Publishers). Examples of the method for introducing a plant expression vector directly into a plant cell include an electroporation method, a gene gun method, a calcium phosphate method, and a polyethylene glycol (PEG) method. These methods are well-known in the art, and a method suitable for a particular plant to be transformed can be suitably selected by those skilled in the art.

A cell transformed by introducing a plant expression vector may be selected based on its drug resistance such as kanamycin resistance. Thereafter, the transformed cell can be regenerated as a plant tissue, a plant organ, and/or a plant body by using a conventional method. Furthermore, seeds can be obtained from the regenerated plant body. Accordingly, a plant having a cell death regulatory gene in its cells can be obtained.

In the plant thus obtained, a DS9-related gene or a part thereof is expressed, whereby cell death of a cell in the plant can be promoted or suppressed.

In a plant in which production of the DS9 or a homologue thereof (i.e., production of a metalloprotease) is decreased, cell death is, generally promoted. In a plant in which the tendency of causing cell death is appropriately enhanced, resistance to a certain kind of environmental stress, in particular, resistance to a pathogen due to the formation of necrotic lesions, can be exhibited. A primary mechanism for this resistance may be explained as follows: cell death is locally promoted, so as to enclose a pathogen growing in an infected region, whereby an infected site can be prevented from spreading. In a natural plant, the mRNA and protein of the DS9 or homologue thereof may be decreased in cells at a site subjected to pathogen infection, so that only the site causes cell death. In a transgenic plant produced so that production of the DS9 or a homologue thereof is decreased, a cell infected with a pathogen is more likely to die. Consequently, the cell death of an infected cell is promoted (i.e., the transgenic plant becomes resistance to the pathogen).

In a plant in which production of the DS9 or a homologue thereof is increased, cell death is generally suppressed. In a plant in which the tendency of causing cell death is appropriately reduced, resistance to various environmental stresses can also be exhibited. When a plant is exposed to environmental stress, an endogenous DS9-related gene can be inactivated. As a result, it becomes difficult to maintain homeostasis of an organelle, and harmful active oxygen can be generated in a plant cell. According to the method of the present invention, production of the DS9 or a homologue thereof can be increased. This leads to an increase in the activity of an metalloprotease, whereby a function of maintaining homeostasis of an organelle (e.g., mitochondria and chloroplast) is improved. Consequently, generation of active oxygen is suppressed to a low level, and cell death is suppressed.

The term "environmental stress" as used herein refers to any stress which may be given to plants in the natural environment to prevent growth thereof. Examples of the environmental stress include pathogen infection, strong light, low temperature, freezing, drying, high temperature, high salt concentration, UV irradiation, ozone, and a herbicide.

The term "conferred resistance" to environmental stress refers to providing a new type of resistance to plants or enhancing the existing resistance of plants.

The term "pathogen infection" refers to infection with a pathogenic factor of a plant, including infection with virus, viroid, filamentous fungi, and bacteria.

The presence of resistance to environmental stress can be confirmed by evaluating the difference which can be observed between a transgenic plant and a control plant when the both plants are put under a certain environmental stress.

For example, disease resistance of a transgenic plant with respect to pathogen infection can be evaluated as the difference in a morphology change between a transgenic plant and a control plant when plants are infected with a pathogen (e.g., virus such as TMV, and filamentous fungi such as *Rhizoctonia solani*). For example, in the case where the degree of necrotic lesions observed in the transgenic plant after pathogen infection is significantly suppressed, compared with the control plant, it is understood that the transgenic plant is conferred with the resistance.

A transgenic plant which is conferred with resistance to pathogen infection in accordance with the present invention includes plants which are resistance at least one of TMV and *Rhizoctonia solani*.

Herbicide resistance of a transgenic plant can be evaluated as resistance to a known herbicide such as a superoxide-generating herbicide (e.g., 1,1-dimethyl-4,4-bipyridinium dichloride; sold under a tradename PARAQUAT). For example, in the case where the degree of decomposition of chlorophyll a and chlorophyll b is significantly suppressed in a transgenic plant after herbicide treatment, compared with a control plant, it is understood that the transgenic plant is conferred with the resistance.

As described above, it is suggested that regulation of cell death by an ATP-dependent Zn-type metalloprotease, such as DS9, is deeply involved in biofunction not only in the plants but also in the eucaryotes in general. Thus, a selective inhibitor of a DS9-related gene may be important as means for selectively suppressing biofunction. For example, such an inhibitor can be utilized as a candidate for an agrochemical or a pharmaceutical.

The screening of a selective inhibitor of a DS9-related gene is conducted by introducing a candidate inhibitor into a plant cell containing a DS9-related gene, and identifying whether or not production of the DS9 or a homologue thereof is selectively decreased in the plant cell. The conditions for performing this screening method can be appropriately selected by those skilled in the art. The screening is performed, for example, by inoculating tobacco having no N gene with TMV, followed by treatment with a candidate inhibitor, and investigating whether or not necrotic lesions are formed in the TMV-infected portion. In the case where necrotic lesions are formed only in the TMV-infected portion of the treated leaf, and no significant change in morphology is recognized in the treated leaf which is not infected with TMV, the candidate inhibitor is determined to be selective for a DS9-related gene.

For example, a plant cell used for the screening can exist in the form of any type of a plant. Preferably, the plant cell is used in vitro as a free plant cell. The plant cell preferably has a DS9-related gene as an endogenous gene. A candidate inhibitor includes, but is not limited to, proteins, nucleic acids, saccharides, and lipids. Appropriate means for delivering the candidate inhibitor to a plant cell can be selected by those skilled in the art depending upon the kind of an inhibitor.

Whether or not production of the DS9 or a homologue thereof is decreased in a plant cell treated with a candidate inhibitor can be appropriately identified by the method well-known to those skilled in the art. For example, it can be easily determined by western blotting analysis by comparing the protein amounts of the DS9 or a homologue thereof between the plant cell treated with a candidate inhibitor and the untreated plant cell. In the case where production of the DS9 or a homologue thereof is significantly decreased in the treated plant cell, it is understood that the candidate inhibitor used is an inhibitor of a DS9-related gene.

Hereinafter, the present invention will be further described in detail by way of the illustrative examples. The restriction enzymes, plasmids and the like used in the following examples are available from commercial sources.

EXAMPLE 1

Isolation of DS9 Gene

*N. tabacum* cv. Samsun NN and Samsun nn were grown in a temperature-controlled greenhouse at 25° C. under 16 hr of light, at an intensity of 120 $\mu E/m^2/s$. OM strain of TMV (Gene bank of National Institute of Agrobiological Resources, Ministry of Agriculture, Forestry and Fisheries, Japan) was used in this example. For the temperature shift assay, a tobacco leaf was inoculated with TMV by gentle rubbing of the upper epidermis of a leaf with a suspension in 10 mM phosphate buffer (pH 7.0) containing the virus at an adequate concentration and wet Carborundum (#600, Kishida Chemicals., Osaka, Japan), and incubated for 30 min at room temperature to allow the virus to invade. After the infected leaf was washed with water to remove Carborundum, the leaf was put into a transparent plastic container which was transferred to an incubator held at 30° C. under 24 hr of light, at an intensity of 60 $\mu E/m^2/s$. After incubating for 48 hr, the container was transfered to an incubator held at 20° C., under 24 hr of light at an intensity of 60 $\mu E/m^2/s$. During the incubation, both at 20° C. and 30° C., water was supplied to a petiole of the leaf by covering with wet tissue paper.

Differential screening was performed as described by Seo et al. (Science, vol. 270, 1988, (1995)). Briefly, tobacco leaves were infected with TMV (10 $\mu g/ml$), incubated at 30° C. and then the tempereture was shifted to 20° C. Poly(A)+ RNA was isolated from the leaves harvested 3 hr or 52 hr after the temperature shift. Two radioactively labelled single-stranded cDNA probes, i.e., a plus probe (prepared from the poly(A)+RNA of 3 hr after the temperature shift) and a minus probe (prepared from the poly(A)+RNA of 52 hr after the temperature shift), were synthesized. These two probes were used to perform differential screening for a cDNA library. The library was prepared by a conventional method from the poly(A)+RNA that were used for synthesis of the plus probe. As a result, 6 clones were found to hybridize the plus probe only. One cDNA was designated as DS9. This cDNA was excised with R408 helper phage and recirclularized to subclone into a pBluescript SK⁻phagemid vector according to the manufacturer's instructions (Stratagene).

Both strands of DS9 were sequenced by the dideoxy chain-termination method using a model 373A DNA sequencer (Applied Biosystems). Nucleic acid and amino acid sequences were analyzed with the GENE WORKS (IntelliGenetics) software system.

Amino acid sequences encoded by DS9 cDNA had 40%, 30%, 80% and 42% homologies with the respective amino acid sequences of FtsH from *E. coli*, Osdlp from yeast, ArFtsH from *Arabidopsis thaliana* and Pftf from red pepper, respectively. Particularly high homologies were found in the ATPase conserved regions. As with the other ATP dependent Zn-type metalloproteases, DS9 had N-terminal hydrophobic regions considered to span a membrane, a central ATPase region, and a C-terminal $Zn^{2+}$-binding motif (FIG. 1).

EXAMPLE 2

Expression of Recombinant GST-DS9 Protein in *E. coli*

To generate GST-DS9 fusion gene, the DS9 coding region (from position 411 to 2240 in SEQ ID NO: 1) was amplified by PCR using primers:. 5'-ACGTGGATCCTTGAATGCTGTGAAAAAGGGTA-3' (SEQ ID NO:8) and 5'-ACGTGAATTCTTATGCCTATTTCTCTTGCATC-3' (SEQ ID NO:9). A BamHI-EcoRI fragment was subcloned into the BamHI and EcoRI sites of pGEX-2T (Pharmacia; Smith and Johnson, Gene, 67, 31 (1988)) so that the DS9 is fused to the C terminus of the GST protein. The resulting construct was sequenced around the linkage site between GST and DS9 regions to confirm that the respective coding regions was linked in-frame. Because almost all of the GST-DS9 fusion protein was produced as an insoluble protein in E. coli, the protein was purified from the insoluble fraction by the following procedures.

The pGEX-DS9 was expressed in E. coli strain JM109 (Stratagene) by incubating with 0.4 mM IPTG for 12 hr. Cells were pelleted, washed and suspended in buffer A (20 mM Tris-HCl, pH 8.0, 30 mM NaCl, 10 mM EDTA, 2 mM phenylmethanesulfonyl fluoride (PMSF)). After addition of 1/10 volume of lysozyme (20 mg/ml in buffer A), the suspension was incubated for 1 hr on ice and cells were disrupted by sonication. The insoluble fraction was collected by centrifugation at 6,000× g for 10 min at 4° C., washed three times with buffer B (20 mM Tris-HCl, pH 7.5, 30 mM NaCl). The insoluble fraction was then collected by centrifugation at 8,000× g for 10 min at 4° C., and resuspended in 10 mM EDTA (pH 8.0).

After addition of 8M guanidine-HCl (pH 8.3) to a final concentration of 6.22M, the lysate was subjected to centrifugation at 12,000× g for 30 min at 4° C. The supernatant was dialyzed first against buffer C (2M guanidine-HCl, 0.2 mM EDTA, pH 8.0, 5 mM β-mercaptoethanol) for 2 hr at 4° C., then against buffer D (20 mM Tris-HCl, pH 7.5, 100 mM NaCl, 0.5 mM EDTA, 5 mM β-mercaptoethanol) for more than 4 hr at 4° C. After collection by centrifugation at 100,000× g for 30 min at 4° C., the supernatant was subjected to affinity purification with glutathioneagarose beads according to the method of Smith and Johnson et. al. (supra). Protein concentrations were determined by a Coomassie dye-based protein assay kit (Bio-Rad).

EXAMPLE 3

ATPase Activity Assay

In order to investigate whether DS9 has ATPase activity, the ATPase activity was measured at 37° C. as described by Armon et. al., (The Journal of Biological Chemistry, 265, 20723 (1990)). To assay the ATP hydrolysis, the reaction mixture (25 µl) contained following components: 50 mM Tris-HCl (pH 7.6), 5 mM $MgCl_2$, 2 mM dithiothreitol (DTT), 1 mM ATP, 1 mM [α-32P]ATP (about 148 TBq/mmol; ICN Biomedicals Inc.), and 6 µg/ml GST-DS9 protein. Radioactivity was determined by a conventional method according to Cerenkiv radiation.

The results are shown in FIG. 2. It was thus shown that the recombinant protein expressed in E. coli had ATPase activity.

EXAMPLE 4

Fluctuation in the DS9 Transcriptional Level After the Temperature Shift

Northern analysis was performed to study fluctuation in the DS9 transcription level after the temperature shift in TMV-infected NN tobacco.

A leaf of tobacco (N. tabacum cv. Samsun NN) was infected with TMV as described in Example 1 and incubated at 30° C. for 40 hr prior to the temperature shift to 20° C. A leaf that had not been infected with TMV but had been wounded was used as a control (mock).

The leaves were collected at 0, 1, 3, 4, 8 and 24 hr after the temperature shift to 20° C., and respective total RNAs were prepared according to the method of Seo et al. (supra).

For the DS9 cDNA, the partial DNA fragment corresponding to the 3' noncoding region of the cDNA was used as a probe.

As control probes, cDNAs encoding acidic PR-1 protein and basic PR-1 protein, which are expressed specifically upon infection were used. A cDNA probe encoding an acidic PR-1 protein was synthesized by PCR as described by Matsuoka et al. (Plant Physiology, 85, 942 (1987)) using primer A: 5'-TACTAATTGAAACGACCTACGTCC-3' (SEQ ID NO:10) primer B: 5'-ATAATAATATCTGATCATACATCAAGC-3' (SEQ ID NO:11) according to the conventional method. A cDNA encoding a basic PR-1 protein (Eyal et al., Plant Molecular Biology 19, 589 (1992)) was synthesized by PCR using synthetic primers (primer A: 5'-ATCCCTTTGATTCCAAGGTTGG-3' (SEQ ID NO:12); primer B: 5'-CAAAACACATACATATACACACCTCC-3' (SEQ ID NO:13)), which were designed from the reported sequence data, according to the conventional method.

Northern hybridization was performed as described in Seo et al. (supra). Each blot was exposed to XAR film (Kodak) at −80° C. for 48 hr using Intensyfying Screen (Kodak). Relative intensity of the DS9 transcript was determined with the NIH Image 1.61 (National Institute of Health) program.

The results are shown in FIG. 3. It was found that transcription of the DS9 gene was suppressed until the HR occurred. The expression level of the DS9 mRNA in a TMV infected leaf decreased within 1 hr after the temperature shift from 30° C. to 20° C. No expression of the DS9 mRNA was detected 8 hr after the temperature shift. On the other hand, transcription of the DS9 gene in a mock infected leaf was consistent and was not suppressed.

EXAMPLE 5

Production of an Anti-DS9 Protein Antibody

For antibody production, two rabbits were subjected to intraperitoneal injection of the recombinant GST-DS9 protein obtained in Example 2 in an amount of 400 µg/rabbit. Three additional injections of each 100 µg/rabbit, were given at 7-day intervals. The antisera were obtained 2 weeks after the last injection and the immunoglobulin fractions were purified by chromatography on a Protein A-sepharose column (Pharmacia). The fractions containing anti-DS9 antibody were dialyzed against PBS (20 mM $KH_2PO_4$, 140 mM NaCl, pH 7.4). The antibody was tested for cross reactivity with DS9 protein on immunoblots containing fractionated total protein of E. coli.

EXAMPLE 6

Fluctuations of a DS9 Protein Amount After the Temperature Shift

Western blotting analysis was performed to investigate the fluctuations of a DS9 protein amount after the temperature shift in TMV-infected NN tobacco.

A leaf of tobacco (N. tabacum cv. Samsun NN) was infected with TMV as described in Example 1 and incubated at 30° C. for 40 hr prior to the temperature shift to 20° C. A leaf that had not been infected with TMV but had been wounded was used as a control (mock).

The leaves were collected at 0, 3, 4, 6 hr (at 0 and 6 hr for the mocks) after the temperature shift to 20° C. A protein sample obtained from the collected leaves by the conventional method was separated by 8% SDS-polyacrylamide gel and transferred to an Immobilon membrane (Millipore) in a solution containing 25 mM Tris, 192 mM glycine and 20% methanol. After blocking with 2% BSA in TBST (20 mM Tris-HCl, pH 7.5, 150 mM NaCl), the membranes were incubated for 1 hr with the anti-DS9 antibody which was prepared in Example 5 (dilution 1:3000). The membrane was extensively washed in TBS containing 0.05% Tween 20, and incubated for 30 min with goat anti-rabbit IgG conjugated with alkaline phosphatase(Organon Teknika Corp., Durham) (dilution 1:2000). The reaction was visualized by hydrolysis of a substrate tetrazolium-5-bromo-4-chloro-3-indolyl phosphate. Relative intensity of the DS9 protein was determined using NIH Image 1.61 (National Institute of Health) program.

The results are shown in FIG. 4. At 4 and 6 hr after the temperature shift to 20° C., the amount of each DS9 protein in the TMV infected leaves decreased to 78% and 62%, respectively. The DS9 protein mass was shown to decrease specifically during the process leading to the occurence of the HR.

EXAMPLE 7

Fluctuation in the DS9 Transcription Level and the Amount of Protein in the TMV-infected NN Tobacco After Treatment with AMD and Heat Prior to the treatments, tobacco leaves were detached, inoculated with TMV (10 μg/ml in a phosphate buffer (pH 7.0)) or mock inoculated (buffer alone), and incubated at 30° C. for 40 hr. For reagent treatment, after the incubation, petioles of the leaves were put into vials containing 0.5 ml of an inhibitor solutions containing AMD (Sigma Chemical Co., St. Louis, Mo., USA) as a 10% (v/v) methanol aqueous solution. The solution was absorbed through the petioles, and sterile water was added to the vials within 1 hr. For heat treatment, a TMV-infected NN tobacco was subjected to heat shock by treating at 50° C. for 2 minutes. Each of the treated leaves was then further incubated at 30° C. Northern analysis and Western blot analysis were performed as described in Examples 4 and 6. In addition, those treated with water were used as controls.

Figure 5:
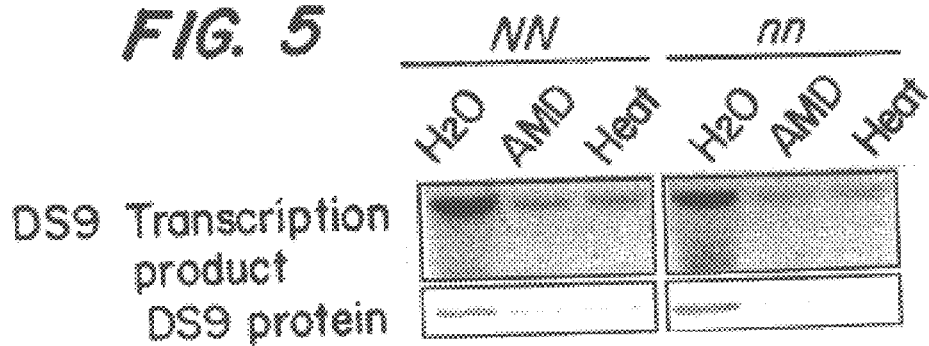
FIG. 5 is an electrophoresis photograph showing the results of northern analysis and western blotting analysis for NN tobacco infected with TMV after treatment with AMD and heat. These analyses exhibit DS9 fluctuations in transcription level and protein amount.
Figure 6A:
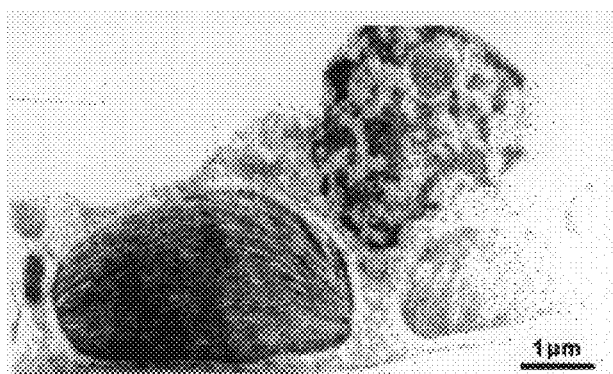
FIGS. 6A to 6D are electron microscope photographs showing chloroplast localization of DS9.
Figure 6B:
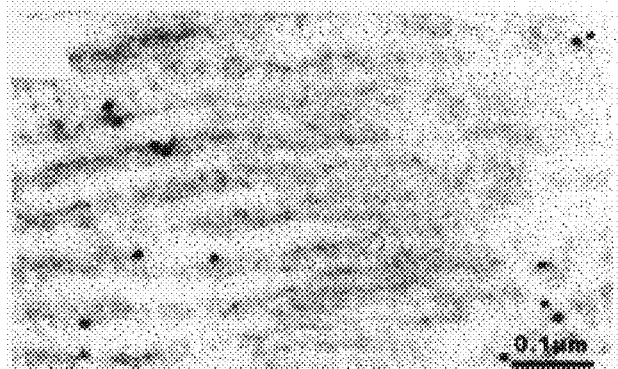
Figure 6C:
Figure 6D:
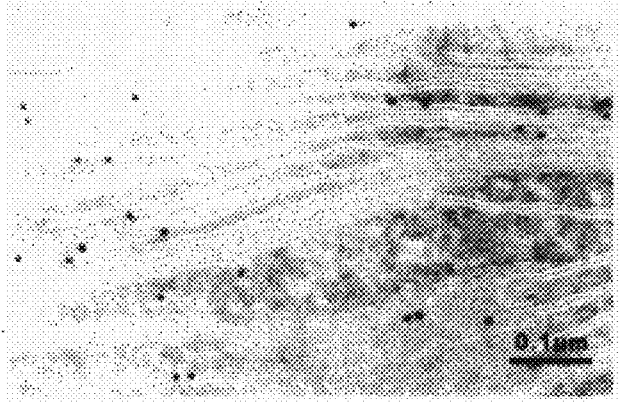

The results are shown in FIG. 5. The AMD and heat treatments which are known to induce the HR, were shown to decrease significantly the DS9 transcription level and the DS9 protein amount in TMV-infected NN tobacco.

EXAMPLE 8

Effects of Various Protease Inhibitors on Induction of Necrotic Lesion Formation The following reagents were used as inhibitors: APMSF, Aprotinin and 3,4-D as serine protease inhibitors, E-64 as a cysteine protease inhibitor, EDTA as a metalloprotease inhibitor, and leupeptin as a serine/cysteine protease inhibitor. Each inhibitor was prepared as described below.

For EDTA (Wako Pure Chemicals. Ind. (Osaka, Japan), an aqueous solution adjusted to pH 8.0 by NaOH was used.

For E-64 (Boehringer Mannheim, Germany), a 50 mM solution in methanol/$H_2O$ (1:1, v/v) was used as a stock solution and subsequently diluted in water to the concentrations indicated below.

For 3,4-D (Boehringer Mannheim, Germany), a 50 mM solution in dimethyl sulfoxide was used as a stock solution and subsequently diluted in water to the concentrations indicated below.

Leupeptin, Aprotinin, and APMSP were each used as an aqueous solution.

In this example, EDTA was used at concentrations of 1 mM, 10 M and 50 mM, and other inhibitors were used at concentrations of 0.01 mM, 0.1 mM and 1 mM.

Prior to reagent treatment, tobacco leaves were detached, inoculated with TMV (8 μg/ml in a phosphate buffer (pH 7.0)) or mock (buffer alone), and incubated at 30° C. for 40 hr. After the incubation, petioles of the leaves were put into vials containing 0.5 ml of inhibitor solutions. The solution was absorbed through the petioles and sterile water was added to the vials within 1 hr. The treated leaves were then further incubated at 30° C. The results are shown in Table 2.

TABLE 2

Effects of various protease inhibitors in induction of necrotic lesion formation[a]

| Inhibitor | Type of inhibitor | Tobacco cv. NN | nn |
|---|---|---|---|
| APMSF | Serine protease | – | – |
| Aprotinin | Serine protease | – | – |
| 3,4-D | Serine protease | – | – |
| E-64 | Cysteine protease | – | – |
| EDTA | metalloprotease | + | + |
| leupeptin | Serine/cysteine protease | – | – |

EDTA was used at concentrations of 1 mM, 10 mM and 50 mM.
Other inhibitors were used at concentratios of 0.01 mM, 0.1 mM and 1 mM.
[a](–) = Necrotic lesion not induced (+) = Necrotic lesion induced A necrotic lesion was induced in NN tobacco when treated with EDTA. A similar necrotic lesion was also observed in nn tobacco containing no N gene. A necrotic lesion was not observed when the other various protease inhibitors were used. These results show that inhibition of the metalloprotease activity, including the activity of the DS9 protein, is sufficient to induce cell death in a plant.

EXAMPLE 9

Localization of DS9 within a Cell (9-1) Immunoelectron microscopy

Immunoelectron microscopy was performed basically as described in Suzuki and Kataoka (Journal of Histochemistry, 40, 379 (1992)) and Tomoyasu et al. (Journal of Bacteriology, 175, 1352 (1993)), except that a leaf was cut into pieces of 1×1 mm and fixed with 0.1% glutaraldehyde and 4% paraformaldehyde in sodium cacodylate (pH 7.4) under vacuum conditions. Then, the leaf tissue was embedded in LR White resin (The London Resin Co., London) and was cut at −20° C. with an ultramicrotome. A section was incubated with anti-DS9 antibody (dilution 1:250) and then reacted with goat anti-rabbit IgG conjugated with 10 nm-gold(dilution 1:100; Biocell Research Laboratories, Cardiff) for 30 min at 37° C. After the immunolabeling, a section was stained with uranyl acetate.

As the cytochemical control, specimen was incubated with non-immunnized rabbit IgG.

For immunoelectron microscopy using ultra-thin frozen sections, some pieces of fixed tissues were infused using the method described in Tokuyasu (Histochemical Journal, 21, 163, 1989) with a mixture of 20% polyvinylpyrrolidone (MW 10,000: Sigma) and 1.6M sucrose, frozen in liquid propane, and then cryo-sectioned. The section was immunogold labelled by the same procedure as for the above described sample embedded with LR White, and adsorption-stained with polyvinyl alcohol (MW 10,000; Sigma). Samples were observed by a transmission electron microscope (H-7100, Hitachi, Japan).

(9-2) Imaging with gold particles

A negative of an electron micrograph was digitized by a flat bed scanner (GT-9000, Epson; 1800 dpi) and stored by TIFF format. The digitized images were normalized to enhance the contrast according to the method of Fukui (Theoretical and Applied Genetics, 72, 27 (1986)) by Adobe Photoshop ver. 3.0 (Adobe Systems, Incorp.). The boundaries of nuclei, chloroplasts, mitochondria and microsomes were traced for each of the electron micrographs, and the areas of the organelles were digitally measured. The number of gold particles were visually counted for each of the organelles.

These results indicated that the DS9 is localized in chloroplasts (see FIG. 6).

EXAMPLE 10

Induction of HR by EDTA and DCMU Treatments

To perform an inhibitor treatment with NN tobacco and nn tobacco, EDTA, a metalloprotease inhibitor, and DCMU (3-(3,4-dichlorophenyl)-1,1-dimethylurea) (Sigma Chemical Co., St Louis, Mo., USA), an inhibitor of electron transport in a photochemical system II (PSII), were used as described in Example 8. An EDTA solution was prepared as described in Example 8. The DCMU was dissolved in methanol. The concentration of the inhibitors were 5 mM and 100 mM, respectively.

After the treatment, leavs were further incubated at 30° C., then examined regarding the followig: formation of a necrotic lesion; expression of PR-1; presence of a marker gene for the HR protein; and accumulation of salicylic acid. For expression of the PR gene, Northern analysis was performed as described in Example 4. Salicylic acid was quantitated as follows.

Figure 7:
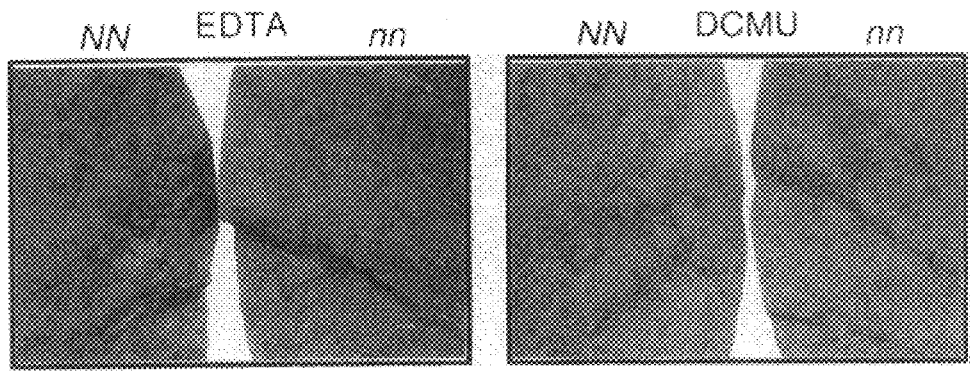
FIG. 7 shows photographs of morphology representing necrotic lesions in tobacco treated as follows: incubating NN and nn tobacco infected with TMV at 30° C. for 40 hours; treating the tobacco with metalloprotein inhibitor (EDTA) and chloroplast electron-transport chain inhibitor (DCMU); and further incubating the tobacco at 30° C. for 24 hours.
Figure 8:
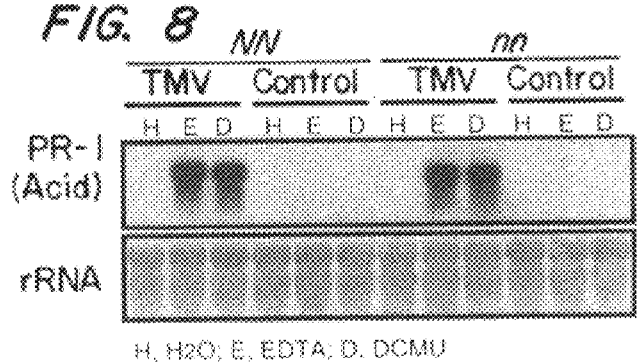
FIG. 8 is an electrophoresis photograph showing the results of northern analysis representing expression levels of PR-1 in tobacco treated as follows: incubating NN and nn tobacco infected with TMV at 30° C. for 40 hours; treating the tobacco with metalloprotein inhibitor (EDTA) and chloroplast electron-transport chain inhibitor (DCMU); and further incubating the tobacco at 30° C. for 24 hours.
Figure 9:
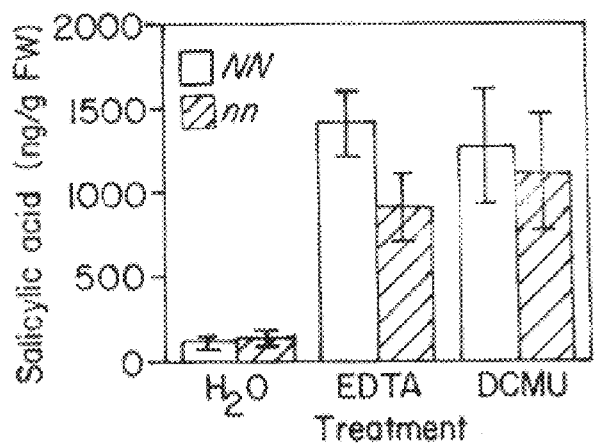
FIG. 9 is a diagram showing the amount of salicylic acid in tobacco treated as follows: incubating NN and nn tobacco infected with TMV at 30° C. for 40 hours; treating the tobacco with metalloprotein inhibitor (EDTA) and chloroplast electron-transport chain inhibitor (DCMU); and further incubating the tobacco at 30° C. for 24 hours.

Free salicylic acid was extracted and quantitated as described by Malamy et al. (The Plant Cell, 4, 359 (1992)). HPLC analysis was performed on a $\mu$Bondasphere, 5-$\mu$m C-18 (3.9 mm×15 cm) column maintained at 40° C. Isocratic separation was conducted with 23% (v/v) methanol in 20 mM sodium acetate (pH 5.0). Fluorescence detection was performed at using a Model RF-550A (Shimazu, Japan) at 1 m/min. All data were corrected for losses. The results are shown in FIGS. 7, 8 and 9. In both NN tobacco and nn tobacco, both EDTA and DCMU induced the HR. It was shown that the HR is induced by inhibition of the metalloprotease or decrease in the chloroplast function.

EXAMPLE 11

Function of a Chloroplast During HR Induction

Figure 10:
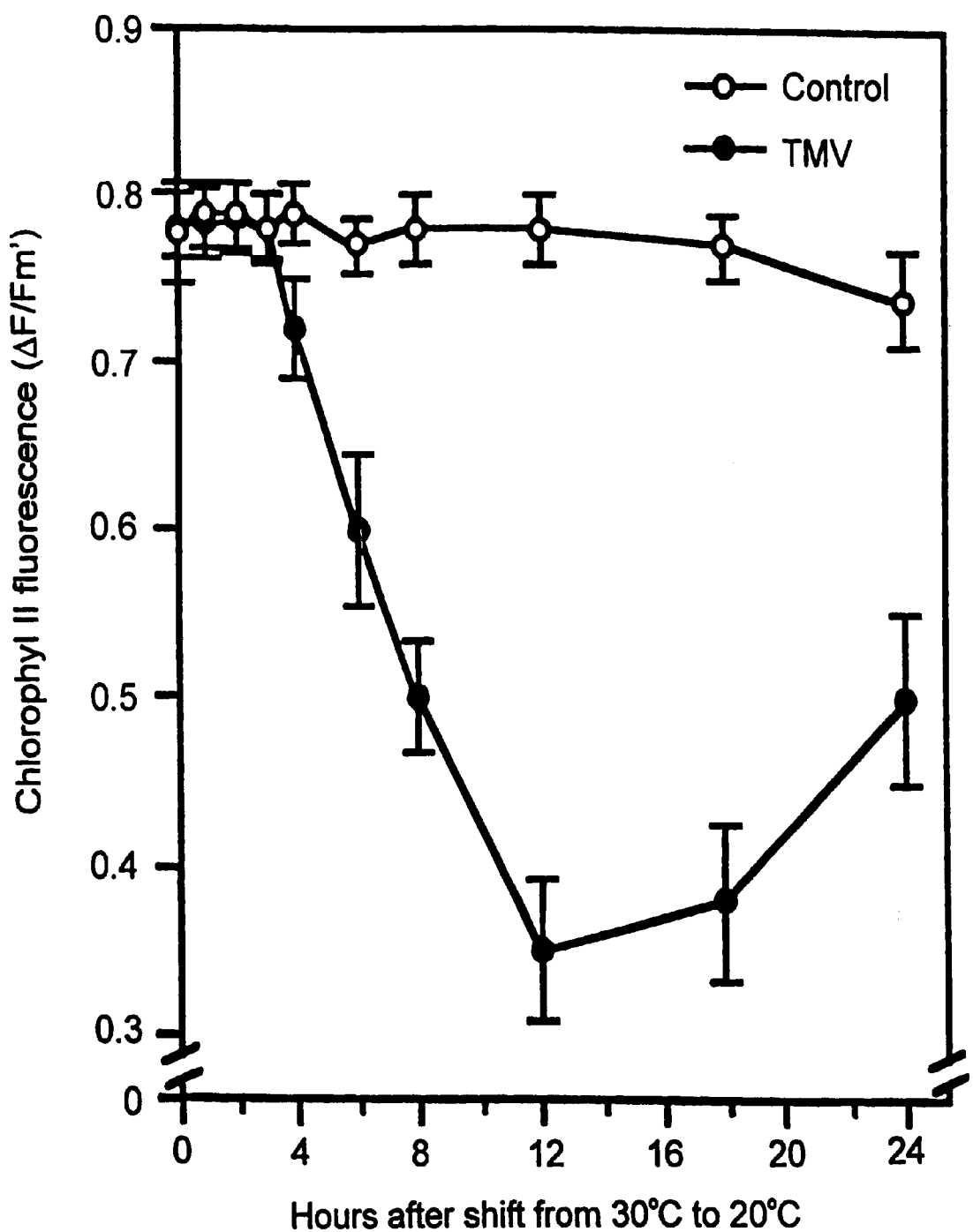
FIG. 10 is a graph showing the decrease in chloroplast function when the HR is induced, measured using PSII activity as an index.

Kinetics of chlorophyll fluorescence induction were measured with pulse amplitude modulation fluorimeter (PAM-2000, Heinz Walz, Germany). TMV infection was performed as described in Example 1. A leaf sample was held so that its surface has an angle of 60° with respect to the direction to the light source, and half of the leaf was exposed to an actinic light (600 $\mu$E/m$^2$/s). The kinetics of fluorescence induction was recorded on a portable computer installed with Data Acquisition Software (DA-2000, Heinz Walz). The results were shown in FIG. 10.

The PSII activity in a leaf of NN tobacco inoculated with TMV did not decrease during incubation at 30° C. However, after 4 hr from the temperature shift to 20° C., the PSII activity started decreasing. This time point is consistent with the time that the DS9 protein mass starts to decrease. The results show that decrease in the chloroplast function correlates with decrease in the DS9 protein amount.

EXAMPLE 12

Generation of Transgenic Plants

The DS9 coding region (positions 21 to 2240 of SEQ NO: 1) was amplified by PCR using primers: primer A, 5'-ACTATGGCCAATTCTCTCTC-3' (SEQ ID NO:14), and primer B, 5'-TTATGCCTATTTCTCTTGCATC-3' (SEQ ID NO:15).

For a sense construct, the BamHI and SacI sites were linked at the 5' ends of primers A and B, respectively. For an anti-sense construct, the SacI and BamHI sites were linked at the 5' ends of primers A and B, respectively.

The resultant PCR products were verified by DNA sequencing. The products were digested with BamHI and SacI and then ligated, in the sense and antisense orientation relative to the CaMV 35S promoter, to a binary vector, pBI121 (Clontech), which had previously been digested with BamHI and SacI. The sense and antisense DS9 expression constructs were introduced into *Agrobacterium tumefaciens* LBA4404 (Ooms et al., Gene, 14, 33 (1981)) by electroporation (Wen-Jun and Forde, Nucleic Acid Research, 17, 8385 (1989)). Transformation of Samsun NN tobacco was performed by the leaf-disc cocultivation method (Horsch et al., Science, 227, 1229 (1985)). Leaf discs were immersed in a bacterial solution, placed in an incubation medium (basal Murashige-Skoog (MS) medium with 3% sucrose and B5 vitamins) containing naphthaleneacetic acid (100 $\mu$g/L) and benzyl amino purine (1 mg/L) for 2 days at 25° C. under continuous illumination of white fluorescence lamp, at an intensity of 120 $\mu$E/m$^2$/s. Laef discs were then transferred to the foregoing incubation medium which further contain 500 $\mu$g/ml carbenicillin. After 2 days, leaf discs were transferred to a selection medium (incubation medium containing 500 $\mu$g/ml carbenicillin and 100 $\mu$g/ml kanamycin).

For generation of a transformant which expresses a sense DS9 gene, a plate containing leaf discs was incubated at 25° C. under 16 hr of light at an intensity of 120 $\mu$E/m$^2$/s. For generation of a transformant which expresses an antisense DS9 gene, incubation was carried our at 25° C. under 24 hr of light at an intensity of 10 $\mu$E/m$^2$/s. Shoots formed in kanamycin-containing medium were transferred to a hormones-less selection medium. After rooting, plantlets were transferred to a pot containing soil.

EXAMPLE 13

Analysis of Cell Death Regulation in Transgenic Plant (TMV infection)

Strains of self-pollinated, second generation were obtained from the transgenic tobacco obtained in Example 12, in which the DS9 cDNA was expressed in sense or in antisense. With these strains, the protein amount was analysed by performing Western blot analysis as described in Example 6. (sense plants; S1, S4, S5, S6, S9; antisense plant; A9, A12) (FIG. 11). In addition, each strain was infected with TMV as described in Example 1, and the size of the lesion caused by the infection was observed (FIGS. 12 and 13). In all experiments, wild type tobacco was used as a control.

In a sense strain (S6) which contains a two-fold amount of the DS9 protein compared to a wild type tobacco, the size of the necrotic lesion reached two-fold the size of that in the wild type. On the other hand, in an antisense strain (A9) which contains about half amount of the DS9 protein compared to a wild type tobacco, the size of necrotic lesion was about a half compared to the wild type. A small necrotic lesion indicates that cell death occurs immediately (i.e. cell death is promoted), thereby spreading of infected plaques is prevented.

These results indicate that cell death is promoted in a cell which contains a smaller amount of the DS9 protein, and suppressed in a cell which contains a larger amount of the DS9 protein. Furthermore, it is apparent that a transgenic tobacco which expresses a DS9 cDNA in an antisense orientation exhibited increased resistance against TMV infection.

(Infection with *Rhizoctonia solani*)

A seed of a self-pollinazed, second generation strain of A9 (a transgenic tobacco obtained in Example 12, which expresses a DS9 cDNA in an antisense orientation) and, as a control, a seed of a tobacco in which a 35S-GUS construct was introduced were obtained. These seeds were each plated in a 9 cm-diameter petri dish containing MS agar medium with 50 µg/ml kanamycin (see Murashige, T. and Skoog, F., "A reversed medium for rapid growth and bioassay with tobacco tissue cultures", Physiologia Plantarum, vol. 15, pp. 473–497(1962)).

Figure 14:
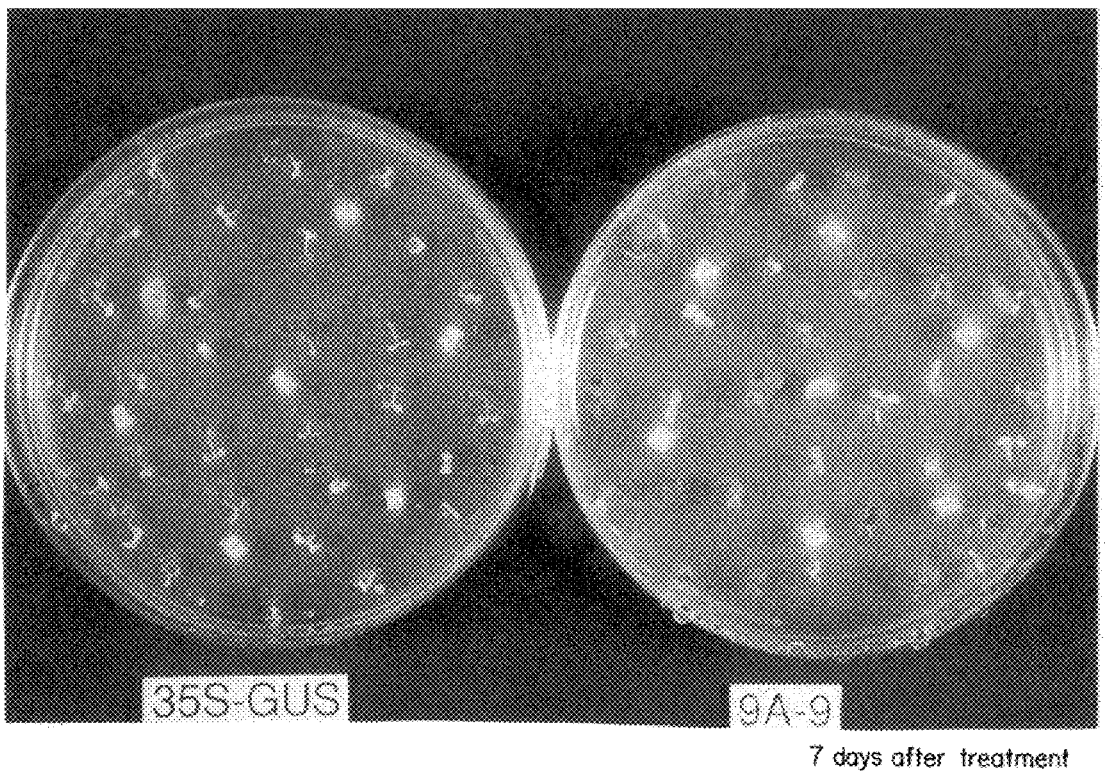
FIG. 14 is a photograph of morphology of a transgenic tobacco (A9) with a DS9 gene introduced thereto in an antisense orientation. The tobacco was observed 7 days after infection with *Rhizoctonia solani*. As a control, a transgenic tobacco with 35S-GUS introduced thereto was used.

*Rhizoctonia solani* was pre-cultured in PDA medium (39 µg/l BACTO™ Potato Dextrose Agar) at 25° C. for 5 days. The flora obtained from the pre-culture were then cut into 3-mm cubic sections, and each section was placed on a petri dish to inoculate 30 seedlings which had been seeded and grown for 7 days in each dish. The dish was then kept at 25° C. After 7 days from plating, green colored surviving plantlets were identified as being resistant. The results are shown in FIG. 14. Survival rates on day 7 were 63% for A9 (19 out of 30 plantlets) and 0% for the controls (0 out of 30 plantlets), respectively.

Thus, a transgenic tobacco which expresses a DS9 cDNA in an antisense orientation exhibited resistance to *Rhizoctonia solani*.

EXAMPLE 14

PARAQUAT (Tradename) Resistance in Transgenic Plants

Figure 15:
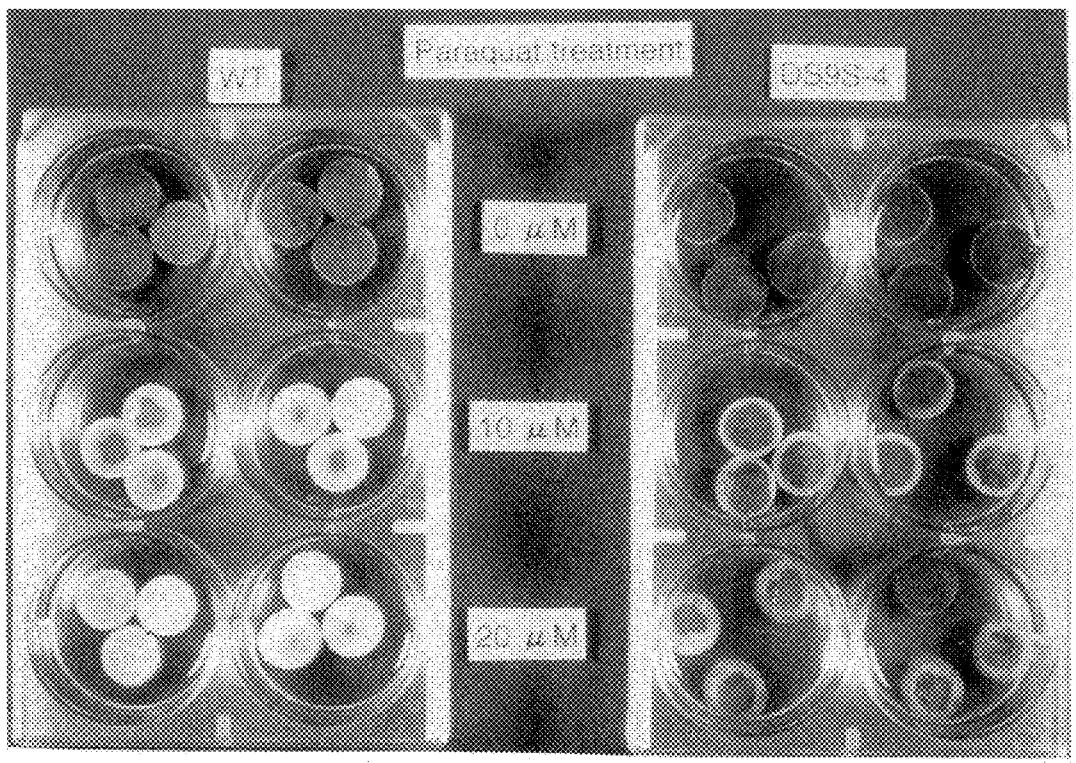
FIG. 15 is a photograph showing morphology of transgenic tobacco (S4) with a DS9 sense gene introduced thereto. The tobacco was observed after paraquat treatment. Wild-type tobacco (WT) was used as a control.

PARAQUAT is a herbicide which generates superoxide in chloroplasts. A transgenic plant S4 (transgenic tobacco which expresses a DS9 cDNA in a sense orientation, obtained in Example 12) and a wild type tobacco (control) were grown in a green house. A tobacco leaf was cut into round pieces, and the leaf discs were immersed in solutions respectively containing 0, 10 and 20 µM PARAQUAT and kept at 25° C., under light of 5000 lux for 45 hr. The results are shown in FIG. 15. A wild type tobacco showed significant change in color into white after PARAQUAT treatment at a concentration of 10 µM, while the S4 plant remained green even after the PARAQUAT treatment at a concentration of 20 µM, indicating significant suppression of chloroplast degradation.

Thus, a transgenic tobacco which expresses a DS9 cDNA in a sense orientation exhibited resistance to PARAQUAT.

According to the present invention, a method for regulating cell death by regulating an expression level of a cell death regulatory gene is provided. Furthermore, a method for producing a plant which is conferred with resistance to various environmental stress by regulating cell death is provided. Thus, a plant useful in terms of agriculture and breeding can be produced. Furthermore, a method for screening a selective inhibitor of a DS9-related gene is provided.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method for promoting or suppressing a hypersensitive response in a plant, comprising the steps of:

transforming a plant cell with a polynucleotide comprising a nucleic acid molecule encoding DS9 having the amino acid sequence of SEQ ID NO:1; and regenerating the transformed plant cell to obtain a plant, wherein the DS9 is an ATP dependent Zn-type metalloprotease, wherein said polynucleotide decreases or increases production of the ATP-dependent Zn-type metalloprotease in cells of the plant, whereby the hypersensitive response in the plant is promoted or suppressed, compared to an untransformed plant.

2. The method of claim 1, wherein the polynucleotide comprises the nucleic acid molecule encoding the DS9 in the antisense orientation, whereby the hypersensitive response in the plant is promoted.

3. A method for producing a plant which has increased resistance to pathogens or superoxide generating herbicides, comprising the steps of:

transforming a plant cell with a polynucleotide comprising a nucleic acid molecule encoding DS9 having the amino acid sequence of SEQ ID NO:1; and regenerating the transformed plant cell to obtain a plant, wherein the DS9 is an ATP-dependent Zn-type metalloprotease, wherein said polynucleotide decreases or increases production of the ATP-dependent Zn-type metalloprotease in cells of the plant, wherein resistance to said pathogens or said herbicides is increased compared to an untransformed plant.

4. The method according to claim 3, wherein the polynucleotide comprises the nucleic acid molecule encoding the DS9 in the antisense orientation.

* * * * *

SEQUENCE LISTING

<160> NUMBER OF SEQ ID NOS: 15

<210> SEQ ID NO 1
<211> LENGTH: 2446
<212> TYPE: DNA
<213> ORGANISM: Nicotiana tabacum
<220> FEATURE:
<221> NAME/KEY: CDS
<222> LOCATION: (21)..(2165)
<223> OTHER INFORMATION: DS9 ATP-dependent Zn-type metalloprotease

<400> SEQUENCE: 1

```
aacaccttcc aaaaatagtt atg gcc aat tct ctc ctc tct tcc aac ttc atg      53
                      Met Ala Asn Ser Leu Leu Ser Ser Asn Phe Met
                       1               5                  10 ggt tct caa atc ttt gtc tct cct ccc acc cct aaa aca aca aag tat     101
Gly Ser Gln Ile Phe Val Ser Pro Pro Thr Pro Lys Thr Thr Lys Tyr
             15                  20                  25 ttc cat ttt cac tcc aaa aga aag tct tta atc cct caa tca att ctc     149
Phe His Phe His Ser Lys Arg Lys Ser Leu Ile Pro Gln Ser Ile Leu
         30                  35                  40 aac aaa aaa ccc aat tca gat aat tca aag aat att cct tca aaa gct     197
Asn Lys Lys Pro Asn Ser Asp Asn Ser Lys Asn Ile Pro Ser Lys Ala
     45                  50                  55
```

```
gct tta gct gct tta ctc ttt tct tca atc act cca cat gcc tat gct    245
Ala Leu Ala Ala Leu Leu Phe Ser Ser Ile Thr Pro His Ala Tyr Ala
 60               65                  70                  75 ctt gat aat act acc cct aca gta cca acc cct caa gtg att caa gct    293
Leu Asp Asn Thr Thr Pro Thr Val Pro Thr Pro Gln Val Ile Gln Ala
                 80                  85                  90 gaa gca gcc aat ccc acc act tca aat cca ttc tct caa aat ata atc    341
Glu Ala Ala Asn Pro Thr Thr Ser Asn Pro Phe Ser Gln Asn Ile Ile
             95                 100                 105 ttg aat gct cca aag cct caa gca cag acc aat cct gaa ctt cca gaa    389
Leu Asn Ala Pro Lys Pro Gln Ala Gln Thr Asn Pro Glu Leu Pro Glu
        110                 115                 120 gtt tct caa tgg aga tac agt gaa ttc ttg aat gct gtg aaa aag ggt    437
Val Ser Gln Trp Arg Tyr Ser Glu Phe Leu Asn Ala Val Lys Lys Gly
    125                 130                 135 aaa gtt gaa agg gtc cga ttc agt aaa gac gga tct gcc ctc ctg ctt    485
Lys Val Glu Arg Val Arg Phe Ser Lys Asp Gly Ser Ala Leu Leu Leu
140                 145                 150                 155 act gct gtt gat ggc cgt aga gct act gta act gtg cct aat gac ccg    533
Thr Ala Val Asp Gly Arg Arg Ala Thr Val Thr Val Pro Asn Asp Pro
                160                 165                 170 gat tta att gac att ttg gct atg aat ggt gtt gat ata tca gtt tct    581
Asp Leu Ile Asp Ile Leu Ala Met Asn Gly Val Asp Ile Ser Val Ser
            175                 180                 185 gaa ggt gat tct gct ggt aat ggg ttg ttt aat tta att gga aat tta    629
Glu Gly Asp Ser Ala Gly Asn Gly Leu Phe Asn Leu Ile Gly Asn Leu
        190                 195                 200 ttc cct ttt att gct ttt gct gga ttg ttc tat ctt ttc cag aga tct    677
Phe Pro Phe Ile Ala Phe Ala Gly Leu Phe Tyr Leu Phe Gln Arg Ser
    205                 210                 215 caa ggt ggg cct ggt ggg cca ggt ggg ctt ggt ggc ccc atg gat ttt    725
Gln Gly Gly Pro Gly Gly Pro Gly Gly Leu Gly Gly Pro Met Asp Phe
220                 225                 230                 235 ggt agg tca aag tca aag ttt caa gaa gtt cct gaa act gga gtg act    773
Gly Arg Ser Lys Ser Lys Phe Gln Glu Val Pro Glu Thr Gly Val Thr
                240                 245                 250 ttt gct gat gtt gct ggt gct gat caa gct aaa ttg gag tta caa gaa    821
Phe Ala Asp Val Ala Gly Ala Asp Gln Ala Lys Leu Glu Leu Gln Glu
            255                 260                 265 gtg gtt gat ttt tta aag aat cct gat aag tat act gct tta ggt gct    869
Val Val Asp Phe Leu Lys Asn Pro Asp Lys Tyr Thr Ala Leu Gly Ala
        270                 275                 280 aaa ata cca aaa ggg tgt ctt ttg gtg gga cca cct ggt aca gga aag    917
Lys Ile Pro Lys Gly Cys Leu Leu Val Gly Pro Pro Gly Thr Gly Lys
    285                 290                 295 aca ctt ttg gct aga gca gtt gct ggt gaa gct ggt gta cca ttt ttc    965
Thr Leu Leu Ala Arg Ala Val Ala Gly Glu Ala Gly Val Pro Phe Phe
300                 305                 310                 315 tca tgt gca gca tca gag ttt gtt gag ttg ttt gtt ggt gtt gga gct   1013
Ser Cys Ala Ala Ser Glu Phe Val Glu Leu Phe Val Gly Val Gly Ala
                320                 325                 330 tct aga gtg agg gat ttg ttc gag aag gcg aag tcg aaa gcg cct tgc   1061
Ser Arg Val Arg Asp Leu Phe Glu Lys Ala Lys Ser Lys Ala Pro Cys
            335                 340                 345 att gtg ttt att gat gag att gat gct gtg ggg agg cag aga ggt gca   1109
Ile Val Phe Ile Asp Glu Ile Asp Ala Val Gly Arg Gln Arg Gly Ala
        350                 355                 360 gga atg gga ggt ggg aat gat gag aga gag cag act att aat caa ctc   1157
Gly Met Gly Gly Gly Asn Asp Glu Arg Glu Gln Thr Ile Asn Gln Leu
```

```
                    365                 370                 375
ttg act gaa atg gat ggg ttt tct gga aat agt gga gta att gtt ttg      1205
Leu Thr Glu Met Asp Gly Phe Ser Gly Asn Ser Gly Val Ile Val Leu
380                 385                 390                 395 gct gca acc aat agg cct gat gtt ctt gat tct gca ttg ttg aga cct      1253
Ala Ala Thr Asn Arg Pro Asp Val Leu Asp Ser Ala Leu Leu Arg Pro
                400                 405                 410 ggg agg ttc gat cga caa gtg act gtc gac agg cct gat gtt gct ggt      1301
Gly Arg Phe Asp Arg Gln Val Thr Val Asp Arg Pro Asp Val Ala Gly
            415                 420                 425 aga atc aag att ctt cag gtg cat tct aga gga aag gcc ctt gca aag      1349
Arg Ile Lys Ile Leu Gln Val His Ser Arg Gly Lys Ala Leu Ala Lys
        430                 435                 440 gat gtg gac ttt gag aag att gcc agg aga aca ccg ggt ttc act ggt      1397
Asp Val Asp Phe Glu Lys Ile Ala Arg Arg Thr Pro Gly Phe Thr Gly
    445                 450                 455 gca gat ttg caa aac ttg atg aat gaa gca gcg atc ctt gca gct agg      1445
Ala Asp Leu Gln Asn Leu Met Asn Glu Ala Ala Ile Leu Ala Ala Arg
460                 465                 470                 475 cgt gaa cta aag gaa ata agt aaa aat gag ata tct gat gct ttg gag      1493
Arg Glu Leu Lys Glu Ile Ser Lys Asn Glu Ile Ser Asp Ala Leu Glu
                480                 485                 490 agg ata att gct gga ccg gag aag aaa aat gct gtt gtc tca gag gag      1541
Arg Ile Ile Ala Gly Pro Glu Lys Lys Asn Ala Val Val Ser Glu Glu
            495                 500                 505 aag aag aag ctg gta gct tat cat gag gcc gcc cat gcc ttg gtt ggt      1589
Lys Lys Lys Leu Val Ala Tyr His Glu Ala Ala His Ala Leu Val Gly
        510                 515                 520 gca ctt atg ccc gag tat gat cct gtt ccc aag ata tct att att cct      1637
Ala Leu Met Pro Glu Tyr Asp Pro Val Pro Lys Ile Ser Ile Ile Pro
    525                 530                 535 cgg ggc caa gct ggt ggt ctt acc ttc ttt gcc cct agc gaa gaa aga      1685
Arg Gly Gln Ala Gly Gly Leu Thr Phe Phe Ala Pro Ser Glu Glu Arg
540                 545                 550                 555 ctt gag tcg ggc ttg tac agc agg agc tac cta gag aat caa atg gca      1733
Leu Glu Ser Gly Leu Tyr Ser Arg Ser Tyr Leu Glu Asn Gln Met Ala
                560                 565                 570 gtt gca ctt ggt gga agg gtt gct gag gag gtt att ttt gga caa gac      1781
Val Ala Leu Gly Gly Arg Val Ala Glu Glu Val Ile Phe Gly Gln Asp
            575                 580                 585 aac gta aca act ggg gca tct aac gat ttc atg ctt gtt tca cga gtg      1829
Asn Val Thr Thr Gly Ala Ser Asn Asp Phe Met Leu Val Ser Arg Val
        590                 595                 600 gca agg cag atg gtt gag aga tta ggg ttc acc aca aag atc gga cag      1877
Ala Arg Gln Met Val Glu Arg Leu Gly Phe Thr Thr Lys Ile Gly Gln
    605                 610                 615 gtt gcc att gga gga ggt gga gga aat cct ttc cta ggt caa cag atg      1925
Val Ala Ile Gly Gly Gly Gly Gly Asn Pro Phe Leu Gly Gln Gln Met
620                 625                 630                 635 tca acc cag aaa gac tac tcc atg gca aca gcc gat gtg gtt gat gct      1973
Ser Thr Gln Lys Asp Tyr Ser Met Ala Thr Ala Asp Val Val Asp Ala
                640                 645                 650 gaa gta agg gaa ttg gtt gaa aga gca tat gaa agg gca aca cag att      2021
Glu Val Arg Glu Leu Val Glu Arg Ala Tyr Glu Arg Ala Thr Gln Ile
            655                 660                 665 atc aca aca cac att gac atc cta cac aag ctt gct cag ctg ttg ata      2069
Ile Thr Thr His Ile Asp Ile Leu His Lys Leu Ala Gln Leu Leu Ile
        670                 675                 680 gag aaa gaa act gtt gat ggt gaa gag ttc atg agc ctt ttc atc gat      2117
```

```
Glu Lys Glu Thr Val Asp Gly Glu Phe Met Ser Leu Phe Ile Asp
    685                 690                 695 ggc aag gcc gag cta tac att tct tgg gtc tct aag gag gag gat       2162
Gly Lys Ala Glu Leu Tyr Ile Ser Trp Val Ser Lys Glu Glu Asp
700                 705                 710 tagtttctgg cttaacaaga cttgatgtat ctggtggttg agagtggtaa attgctgatg 2222 caagagaaat aggcataata catagtgctt tagactgaag aaattgcatt gcagaaccaa 2282 cattttcttc cataagtttg gccacttgcc tttctgtacc atcacttgac cacttttccc 2342 aggctggttg gttatttcca acttcactgc tctcttccta aataagacaa gccacaaaaa 2402 gggataaatt attaattgat aggttggaca attctgcaaa aaaa                 2446

<210> SEQ ID NO 2
<211> LENGTH: 714
<212> TYPE: PRT
<213> ORGANISM: Nicotiana tabacum

<400> SEQUENCE: 2

Met Ala Asn Ser Leu Leu Ser Ser Asn Phe Met Gly Ser Gln Ile Phe
  1               5                  10                  15

Val Ser Pro Thr Pro Lys Thr Thr Lys Tyr Phe His Phe His Ser
                 20                  25                  30

Lys Arg Lys Ser Leu Ile Pro Gln Ser Ile Leu Asn Lys Lys Pro Asn
             35                  40                  45

Ser Asp Asn Ser Lys Asn Ile Pro Ser Lys Ala Ala Leu Ala Ala Leu
         50                  55                  60

Leu Phe Ser Ser Ile Thr Pro His Ala Tyr Ala Leu Asp Asn Thr Thr
 65                  70                  75                  80

Pro Thr Val Pro Thr Pro Gln Val Ile Gln Ala Glu Ala Ala Asn Pro
                     85                  90                  95

Thr Thr Ser Asn Pro Phe Ser Gln Asn Ile Ile Leu Asn Ala Pro Lys
                100                 105                 110

Pro Gln Ala Gln Thr Asn Pro Glu Leu Pro Glu Val Ser Gln Trp Arg
            115                 120                 125

Tyr Ser Glu Phe Leu Asn Ala Val Lys Lys Gly Lys Val Glu Arg Val
        130                 135                 140

Arg Phe Ser Lys Asp Gly Ser Ala Leu Leu Leu Thr Ala Val Asp Gly
145                 150                 155                 160

Arg Arg Ala Thr Val Thr Val Pro Asn Asp Pro Asp Leu Ile Asp Ile
                165                 170                 175

Leu Ala Met Asn Gly Val Asp Ile Ser Val Ser Glu Gly Asp Ser Ala
            180                 185                 190

Gly Asn Gly Leu Phe Asn Leu Ile Gly Asn Leu Phe Pro Phe Ile Ala
        195                 200                 205

Phe Ala Gly Leu Phe Tyr Leu Phe Gln Arg Ser Gln Gly Gly Pro Gly
    210                 215                 220

Gly Pro Gly Gly Leu Gly Gly Pro Met Asp Phe Gly Arg Ser Lys Ser
225                 230                 235                 240

Lys Phe Gln Glu Val Pro Glu Thr Gly Val Thr Phe Ala Asp Val Ala
                245                 250                 255

Gly Ala Asp Gln Ala Lys Leu Glu Leu Gln Glu Val Val Asp Phe Leu
            260                 265                 270

Lys Asn Pro Asp Lys Tyr Thr Ala Leu Gly Ala Lys Ile Pro Lys Gly
        275                 280                 285
```

```
Cys Leu Leu Val Gly Pro Pro Gly Thr Gly Lys Thr Leu Leu Ala Arg
290                 295                 300
Ala Val Ala Gly Glu Ala Gly Val Pro Phe Phe Ser Cys Ala Ala Ser
305                 310                 315                 320
Glu Phe Val Glu Leu Phe Val Gly Val Gly Ala Ser Arg Val Arg Asp
                325                 330                 335
Leu Phe Glu Lys Ala Lys Ser Lys Ala Pro Cys Ile Val Phe Ile Asp
            340                 345                 350
Glu Ile Asp Ala Val Gly Arg Gln Arg Gly Ala Gly Met Gly Gly Gly
            355                 360                 365
Asn Asp Glu Arg Glu Gln Thr Ile Asn Gln Leu Leu Thr Glu Met Asp
370                 375                 380
Gly Phe Ser Gly Asn Ser Gly Val Ile Val Leu Ala Ala Thr Asn Arg
385                 390                 395                 400
Pro Asp Val Leu Asp Ser Ala Leu Leu Arg Pro Gly Arg Phe Asp Arg
                405                 410                 415
Gln Val Thr Val Asp Arg Pro Asp Val Ala Gly Arg Ile Lys Ile Leu
            420                 425                 430
Gln Val His Ser Arg Gly Lys Ala Leu Ala Lys Asp Val Asp Phe Glu
            435                 440                 445
Lys Ile Ala Arg Arg Thr Pro Gly Phe Thr Gly Ala Asp Leu Gln Asn
450                 455                 460
Leu Met Asn Glu Ala Ala Ile Leu Ala Ala Arg Arg Glu Leu Lys Glu
465                 470                 475                 480
Ile Ser Lys Asn Glu Ile Ser Asp Ala Leu Glu Arg Ile Ile Ala Gly
                485                 490                 495
Pro Glu Lys Lys Asn Ala Val Val Ser Glu Lys Lys Leu Val
            500                 505                 510
Ala Tyr His Glu Ala Ala His Ala Leu Val Gly Ala Leu Met Pro Glu
            515                 520                 525
Tyr Asp Pro Val Pro Lys Ile Ser Ile Ile Pro Arg Gly Gln Ala Gly
530                 535                 540
Gly Leu Thr Phe Phe Ala Pro Ser Glu Glu Arg Leu Glu Ser Gly Leu
545                 550                 555                 560
Tyr Ser Arg Ser Tyr Leu Glu Asn Gln Met Ala Val Ala Leu Gly Gly
                565                 570                 575
Arg Val Ala Glu Glu Val Ile Phe Gly Gln Asp Asn Val Thr Thr Gly
            580                 585                 590
Ala Ser Asn Asp Phe Met Leu Val Ser Arg Val Ala Arg Gln Met Val
            595                 600                 605
Glu Arg Leu Gly Phe Thr Thr Lys Ile Gly Gln Val Ala Ile Gly Gly
            610                 615                 620
Gly Gly Gly Asn Pro Phe Leu Gly Gln Gln Met Ser Thr Gln Lys Asp
625                 630                 635                 640
Tyr Ser Met Ala Thr Ala Asp Val Val Asp Ala Glu Val Arg Glu Leu
                645                 650                 655
Val Glu Arg Ala Tyr Glu Arg Ala Thr Gln Ile Ile Thr Thr His Ile
            660                 665                 670
Asp Ile Leu His Lys Leu Ala Gln Leu Leu Ile Glu Lys Glu Thr Val
            675                 680                 685
Asp Gly Glu Glu Phe Met Ser Leu Phe Ile Asp Gly Lys Ala Glu Leu
690                 695                 700
Tyr Ile Ser Trp Val Ser Lys Glu Glu Asp
```

<210> SEQ ID NO 3
<211> LENGTH: 300
<212> TYPE: PRT
<213> ORGANISM: Nicotiana tabacum
<220> FEATURE:
<223> OTHER INFORMATION: DS9 (positions 273-572)

<400> SEQUENCE: 3

Lys Asn Pro Asp Lys Tyr Thr Ala Leu Gly Ala Lys Ile Pro Lys Gly
 1               5                  10                  15
Cys Leu Leu Val Gly Pro Pro Thr Gly Lys Thr Leu Leu Ala Arg
            20                  25                  30
Ala Val Ala Gly Glu Ala Gly Val Pro Phe Phe Ser Cys Ala Ala Ser
            35                  40                  45
Glu Phe Val Glu Leu Phe Val Gly Val Gly Ala Ser Arg Val Arg Asp
        50                  55                  60
Leu Phe Glu Lys Ala Lys Ser Lys Ala Pro Cys Ile Val Phe Ile Asp
 65                  70                  75                  80
Glu Ile Asp Ala Val Gly Arg Gln Arg Gly Ala Gly Met Gly Gly Gly
                 85                  90                  95
Asn Asp Glu Arg Glu Gln Thr Ile Asn Gln Leu Leu Thr Glu Met Asp
            100                 105                 110
Gly Phe Ser Gly Asn Ser Gly Val Ile Val Leu Ala Ala Thr Asn Arg
        115                 120                 125
Pro Asp Val Leu Asp Ser Ala Leu Leu Arg Pro Gly Arg Phe Asp Arg
    130                 135                 140
Gln Val Thr Val Asp Arg Pro Asp Val Ala Gly Arg Ile Lys Ile Leu
145                 150                 155                 160
Gln Val His Ser Arg Gly Lys Ala Leu Ala Lys Asp Val Asp Phe Glu
                165                 170                 175
Lys Ile Ala Arg Arg Thr Pro Gly Phe Thr Gly Ala Asp Leu Gln Asn
            180                 185                 190
Leu Met Asn Glu Ala Ala Ile Leu Ala Ala Arg Arg Glu Leu Lys Glu
        195                 200                 205
Ile Ser Lys Asn Glu Ile Ser Asp Ala Leu Glu Arg Ile Ile Ala Gly
    210                 215                 220
Pro Glu Lys Lys Asn Ala Val Val Ser Glu Glu Lys Lys Lys Leu Val
225                 230                 235                 240
Ala Tyr His Glu Ala Ala His Ala Leu Val Gly Ala Leu Met Pro Glu
                245                 250                 255
Tyr Asp Pro Val Pro Lys Ile Ser Ile Ile Pro Arg Gly Gln Ala Gly
            260                 265                 270
Gly Leu Thr Phe Phe Ala Pro Ser Glu Glu Arg Leu Glu Ser Gly Leu
        275                 280                 285
Tyr Ser Arg Ser Tyr Leu Glu Asn Gln Met Ala Val
    290                 295                 300

<210> SEQ ID NO 4
<211> LENGTH: 300
<212> TYPE: PRT
<213> ORGANISM: Arabidopsis thaliana
<220> FEATURE:
<223> OTHER INFORMATION: ArFtsH (positions 282-581)

<400> SEQUENCE: 4

```
Lys Asn Pro Asp Lys Tyr Thr Ala Leu Gly Ala Lys Ile Pro Lys Gly
 1               5                  10                  15

Cys Leu Leu Val Gly Pro Pro Gly Thr Gly Lys Thr Leu Leu Ala Arg
            20                  25                  30

Ala Val Ala Gly Glu Ala Gly Val Pro Phe Phe Ser Ser Arg Pro Gln
        35                  40                  45

Glu Phe Val Glu Leu Phe Val Gly Val Gly Ala Ser Arg Val Arg Asp
    50                  55                  60

Leu Phe Glu Lys Ala Lys Ser Lys Ala Pro Cys Ile Val Phe Ile Asp
65                  70                  75                  80

Glu Ile Asp Ala Val Gly Arg Gln Arg Gly Ala Gly Met Gly Gly Gly
                85                  90                  95

Asn Asp Glu Arg Glu Gln Thr Ile Asn Gln Leu Leu Thr Glu Met Asp
            100                 105                 110

Gly Phe Ser Gly Asn Ser Gly Val Ile Val Leu Ala Ala Thr Asn Arg
        115                 120                 125

Pro Asp Val Leu Asp Ser Ala Leu Leu Arg Pro Gly Arg Phe Asp Arg
    130                 135                 140

Gln Val Thr Val Asp Arg Pro Asp Val Ala Gly Arg Val Lys Ile Leu
145                 150                 155                 160

Gln Val His Ser Arg Gly Lys Ala Leu Gly Lys Asp Val Asp Phe Asp
                165                 170                 175

Lys Val Ala Arg Arg Thr Pro Gly Phe Thr Gly Ala Asp Leu Gln Asn
            180                 185                 190

Leu Met Asn Glu Ala Ala Ile Leu Ala Ala Arg Arg Asp Val Lys Glu
        195                 200                 205

Ile Ser Lys Asp Glu Ile Ser Asp Ala Leu Glu Arg Ile Ile Ala Gly
    210                 215                 220

Pro Glu Lys Lys Asn Ala Val Val Ser Glu Glu Lys Lys Arg Leu Val
225                 230                 235                 240

Ala Tyr His Glu Ala Gly His Ala Leu Val Gly Ala Leu Met Pro Glu
                245                 250                 255

Tyr Asp Pro Val Ala Lys Ile Ser Ile Ile Pro Arg Gly Gln Ala Gly
            260                 265                 270

Gly Leu Thr Phe Phe Ala Pro Ser Glu Glu Arg Leu Glu Ser Gly Leu
        275                 280                 285

Tyr Ser Arg Ser Tyr Leu Glu Asn Gln Met Ala Val
    290                 295                 300

<210> SEQ ID NO 5
<211> LENGTH: 297
<212> TYPE: PRT
<213> ORGANISM: Escherichia coli
<220> FEATURE:
<223> OTHER INFORMATION: FtsH (positions 172-468)

<400> SEQUENCE: 5

Arg Glu Pro Ser Arg Phe Gln Lys Leu Gly Gly Lys Ile Pro Lys Gly
 1               5                  10                  15

Val Leu Met Val Gly Pro Pro Gly Thr Gly Lys Thr Leu Leu Ala Lys
            20                  25                  30

Ala Ile Ala Gly Glu Ala Lys Val Pro Phe Phe Thr Ile Ser Gly Ser
        35                  40                  45

Asp Phe Val Glu Met Phe Val Gly Val Gly Ala Ser Arg Val Arg Asp
    50                  55                  60
```

-continued

```
Met Phe Glu Gln Ala Lys Lys Ala Ala Pro Cys Ile Ile Phe Ile Asp
 65                  70                  75                  80

Glu Ile Asp Ala Val Gly Arg Gln Arg Gly Ala Gly Leu Gly Gly Gly
                 85                  90                  95

His Asp Glu Arg Glu Gln Thr Ile Asn Gln Met Leu Val Glu Met Asp
            100                 105                 110

Gly Phe Glu Gly Asn Glu Gly Ile Ile Val Ile Ala Ala Thr Asn Arg
        115                 120                 125

Pro Asp Val Leu Asp Pro Ala Leu Leu Arg Pro Gly Arg Phe Asp Arg
    130                 135                 140

Gln Val Val Val Gly Leu Pro Asp Val Arg Gly Arg Glu Gln Ile Leu
145                 150                 155                 160

Lys Val His Met Arg Arg Val Pro Leu Ala Pro Asp Ile Asp Ala Ala
                165                 170                 175

Ile Ile Ala Arg Gly Thr Pro Gly Phe Ser Gly Ala Asp Leu Ala Asn
            180                 185                 190

Leu Val Asn Glu Ala Ala Leu Phe Ala Ala Arg Gly Asn Lys Arg Val
        195                 200                 205

Val Ser Met Val Glu Phe Glu Lys Ala Lys Asp Lys Ile Met Met Gly
    210                 215                 220

Ala Glu Arg Arg Ser Met Val Met Thr Glu Ala Gln Lys Glu Ser Thr
225                 230                 235                 240

Ala Tyr His Glu Ala Gly His Ala Ile Ile Gly Arg Leu Val Pro Glu
                245                 250                 255

His Asp Pro Val His Lys Val Thr Ile Ile Pro Arg Gly Arg Ala Leu
            260                 265                 270

Gly Val Thr Phe Phe Leu Pro Glu Gly Asp Ala Ile Ser Ala Ser Arg
        275                 280                 285

Gln Lys Leu Glu Ser Gln Ile Ser Thr
    290                 295

<210> SEQ ID NO 6
<211> LENGTH: 294
<212> TYPE: PRT
<213> ORGANISM: Saccharomyces cerevisiae
<220> FEATURE:
<223> OTHER INFORMATION: yeast Osd1p (positions 301-594)

<400> SEQUENCE: 6

Lys Asp Pro Thr Lys Tyr Glu Ser Leu Gly Gly Lys Leu Pro Lys Gly
  1               5                  10                  15

Val Leu Leu Thr Gly Pro Pro Gly Thr Gly Lys Thr Leu Leu Ala Arg
                 20                  25                  30

Ala Thr Ala Gly Glu Ala Gly Val Asp Phe Phe Met Ser Gly Ser
             35                  40                  45

Glu Phe Asp Glu Val Tyr Val Gly Val Gly Ala Lys Arg Ile Arg Asp
         50                  55                  60

Leu Phe Ala Gln Ala Arg Ser Arg Ala Pro Ala Ile Ile Phe Ile Asp
 65                  70                  75                  80

Glu Leu Asp Ala Ile Gly Gly Lys Arg Asn Pro Lys Asp Gln Ala Tyr
                 85                  90                  95

Ala Lys Gln Thr Leu Asn Gln Leu Leu Val Glu Leu Asp Gly Phe Ser
            100                 105                 110

Gln Thr Ser Gly Ile Ile Ile Ile Gly Ala Thr Asn Phe Pro Glu Ala
        115                 120                 125
```

-continued

```
Leu Asp Lys Ala Leu Leu Arg Pro Gly Arg Phe Asp Lys Val Val Asn
    130                 135                 140

Val Asp Leu Pro Asp Val Arg Gly Arg Ala Asp Ile Leu Lys His His
145                 150                 155                 160

Met Lys Lys Ile Thr Leu Ala Asp Asn Val Asp Pro Thr Ile Ile Ala
                165                 170                 175

Arg Gly Thr Pro Gly Leu Ser Gly Ala Glu Leu Ala Asn Leu Val Asn
            180                 185                 190

Gln Ala Ala Val Tyr Ala Cys Gln Lys Asn Ala Val Ser Val Asp Met
        195                 200                 205

Ser His Phe Glu Trp Ala Lys Asp Lys Ile Leu Met Gly Ala Glu Arg
    210                 215                 220

Lys Thr Met Val Leu Thr Asp Ala Ala Arg Lys Ala Thr Ala Phe His
225                 230                 235                 240

Glu Ala Gly His Ala Ile Met Ala Lys Tyr Thr Asn Gly Ala Thr Pro
                245                 250                 255

Leu Tyr Lys Ala Thr Ile Leu Pro Arg Gly Arg Ala Leu Gly Ile Thr
            260                 265                 270

Phe Gln Leu Pro Glu Met Asp Lys Val Asp Ile Thr Lys Arg Glu Cys
        275                 280                 285

Gln Ala Arg Leu Asp Val
    290

<210> SEQ ID NO 7
<211> LENGTH: 296
<212> TYPE: PRT
<213> ORGANISM: Capsicum sp.
<220> FEATURE:
<223> OTHER INFORMATION: red pepper Pftf (positions 250-545)

<400> SEQUENCE: 7

Lys Lys Pro Glu Arg Phe Thr Ala Val Gly Ala Arg Ile Pro Lys Gly
  1               5                  10                  15

Val Leu Leu Val Gly Pro Pro Gly Thr Gly Lys Thr Leu Leu Ala Lys
                20                  25                  30

Ala Ile Ala Gly Glu Ala Gly Val Pro Phe Phe Ser Ile Ser Gly Ser
            35                  40                  45

Glu Phe Val Glu Met Phe Val Gly Val Gly Ala Ser Arg Val Arg Asp
        50                  55                  60

Leu Phe Lys Lys Ala Lys Glu Asn Ala Pro Cys Ile Val Phe Val Asp
65                  70                  75                  80

Glu Ile Asp Ala Val Gly Arg Gln Arg Gly Thr Gly Ile Gly Gly Gly
                85                  90                  95

Asn Asp Glu Arg Glu Gln Thr Leu Asn Gln Leu Leu Thr Glu Met Asp
            100                 105                 110

Gly Phe Glu Gly Asn Thr Gly Ile Ile Val Val Ala Ala Thr Asn Arg
        115                 120                 125

Ala Asp Ile Leu Asp Ser Ala Leu Leu Arg Pro Gly Arg Phe Asp Arg
130                 135                 140

Gln Val Ser Val Asp Val Pro Asp Ile Lys Gly Arg Thr Glu Ile Leu
145                 150                 155                 160

Lys Val His Ala Gly Asn Lys Lys Phe Asp Ser Asp Val Ser Leu Glu
                165                 170                 175

Val Ile Ala Met Arg Thr Pro Gly Phe Ser Gly Ala Asp Leu Ala Asn
            180                 185                 190
```

Leu Leu Asn Glu Ala Ala Ile Leu Ala Gly Arg Arg Gly Lys Thr Ala
        195                 200                 205

Ile Ala Ser Lys Glu Ile Asp Asp Ser Ile Asp Arg Ile Val Ala Gly
    210                 215                 220

Met Glu Gly Thr Val Met Thr Asp Gly Lys Ser Lys Ser Leu Val Ala
225                 230                 235                 240

Tyr His Glu Val Gly His Ala Ile Cys Gly Thr Leu Thr Pro Gly His
            245                 250                 255

Asp Pro Val Gln Lys Val Thr Leu Ile Pro Arg Gly Gln Ala Lys Gly
        260                 265                 270

Leu Thr Trp Phe Ile Pro Ala Asp Asp Pro Thr Leu Ile Ser Lys Gln
    275                 280                 285

Gln Leu Phe Ala Arg Ile Val Gly
    290                 295

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence:PCR primer
      for GST-DS9 fusion gene

<400> SEQUENCE: 8
acgtggatcc ttgaatgctg tgaaaaaggg ta                                     32

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence:PCR primer
      for GST-DS9 fusion gene

<400> SEQUENCE: 9
acgtgaattc ttatgcctat ttctcttgca tc                                     32

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:PCR primer A
      for acidic PR-1 protein cDNA

<400> SEQUENCE: 10
tactaattga aacgacctac gtcc                                              24

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:PCR primer B
      for acidic PR-1 protein cDNA

<400> SEQUENCE: 11
ataataatat ctgatcatac atcaagc                                           27

<210> SEQ ID NO 12
<211> LENGTH: 22
<212> TYPE: DNA
<213> ORGANISM: Artificial Sequence
<220> FEATURE:

```
<223> OTHER INFORMATION: Description of Artificial Sequence:PCR primer A
      for basic PR-1 protein cDNA

<400> SEQUENCE: 12
atccctttga ttccaaggtt gg                                              22

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:PCR primer B
      for basic PR-1 protein cDNA

<400> SEQUENCE: 13
caaaacacat acatatacac acctcc                                          26

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:PCR primer A
      for DS9 coding region

<400> SEQUENCE: 14
actatggcca attctctctc                                                 20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence:PCR primer B
      for DS9 coding region

<400> SEQUENCE: 15
ttatgcctat ttctcttgca tc                                              22
```